(12) United States Patent
Tokonami et al.

(10) Patent No.: US 9,797,842 B2
(45) Date of Patent: Oct. 24, 2017

(54) DEVICE AND METHOD UTILIZING A METALLIC NANOPARTICLE ASSEMBLY STRUCTURE FOR DETECTING A TARGET SUBSTANCE

(75) Inventors: Shiho Tokonami, Sakai (JP); Takuya Iida, Sakai (JP); Yojiro Yamamoto, Sakai (JP); Hiroshi Shiigi, Sakai (JP); Tsutomu Nagaoka, Sakai (JP)

(73) Assignee: OSAKA PREFECTURE UNIVERSITY PUBLIC CORPORATION, Sakai-Shi, Osaka (JP)

( * ) Notice: Subject to any disclaimer, the term of this patent is extended or adjusted under 35 U.S.C. 154(b) by 629 days.

(21) Appl. No.: 13/992,475

(22) PCT Filed: Dec. 8, 2011

(86) PCT No.: PCT/JP2011/078438
§ 371 (c)(1),
(2), (4) Date: Jun. 7, 2013

(87) PCT Pub. No.: WO2012/077756
PCT Pub. Date: Jun. 14, 2012

(65) Prior Publication Data
US 2013/0252275 A1 Sep. 26, 2013

(30) Foreign Application Priority Data
Dec. 8, 2010 (JP) ................. 2010-273284

(51) Int. Cl.
*G01N 21/65* (2006.01)
*G01N 21/552* (2014.01)
*G01N 33/543* (2006.01)

(52) U.S. Cl.
CPC ......... *G01N 21/658* (2013.01); *G01N 21/554* (2013.01); *G01N 33/54346* (2013.01)

(58) Field of Classification Search
CPC ............... G01N 21/658; G01N 21/554; G01N 33/54346
See application file for complete search history.

(56) References Cited

U.S. PATENT DOCUMENTS

2002/0187504 A1* 12/2002 Reich ..................... C12N 11/14
435/6.19
2006/0034729 A1* 2/2006 Poponin ............... G01N 21/658
422/82.05

(Continued)

FOREIGN PATENT DOCUMENTS

JP 2005-533246 A 11/2005
JP 2007-514169 A 5/2007

(Continued)

OTHER PUBLICATIONS

Willets et al., Localized Surface Plasmon Resonance Spectroscopy and Sensing, 2007, The Annual Review of Physical Chemistry, 58:267-297.*

(Continued)

*Primary Examiner* — Melanie Y Brown
(74) *Attorney, Agent, or Firm* — Birch, Stewart, Kolasch & Birch, LLP

(57) ABSTRACT

Disclosed is a device and method allowing a trace amount of a target substance to be detected. A metallic nanoparticle assembly structure is formed of metallic nanoparticles assembled together and modified with a host molecule allowing the target substance to specifically adhere thereto. A metallic nanorod is modified with a host molecule allowing the target substance to specifically adhere thereto. The metallic nanorod is conjugated to the metallic nanoparticle assembly structure by the target substance. An extinction spectrum of localized surface plasmon resonance or a surface enhanced Raman scattering (SERS) spectrum induced in the metallic nanoparticle assembly structure and the (Continued)

metallic nanostructure is measured with a spectroscope. The target substance is detected based on that spectrum.

7 Claims, 25 Drawing Sheets

(56) References Cited

U.S. PATENT DOCUMENTS

| | | | |
|---|---|---|---|
| 2010/0009338 A1 | 1/2010 | Zhang et al. | |
| 2010/0167958 A1* | 7/2010 | Lin | B82Y 5/00 |
| | | | 506/30 |
| 2010/0285490 A1* | 11/2010 | Dees | G01N 33/54373 |
| | | | 435/7.1 |
| 2011/0003320 A1 | 1/2011 | Ito et al. | |
| 2011/0116093 A1* | 5/2011 | Liu | G01N 21/0303 |
| | | | 356/432 |
| 2011/0275061 A1* | 11/2011 | Weidemaier | G01N 21/658 |
| | | | 435/6.1 |
| 2011/0281320 A1 | 11/2011 | Saito et al. | |

FOREIGN PATENT DOCUMENTS

| | | |
|---|---|---|
| JP | 2008-538414 A | 10/2008 |
| JP | 2009-150708 A | 7/2009 |
| JP | 2009-210505 A | 9/2009 |
| JP | 2010-525333 A | 7/2010 |
| WO | WO 2004/007767 A2 | 1/2004 |
| WO | WO 2005/090948 A2 | 9/2005 |
| WO | WO 2006-111414 A1 | 10/2006 |
| WO | WO 2007/040219 A1 | 4/2007 |
| WO | WO 2009/009198 A2 | 1/2009 |
| WO | WO 2010/087121 A1 | 8/2010 |

OTHER PUBLICATIONS

Japanese Notice of Allowance dated Sep. 15, 2015, for Japanese Application No. 2012-547909 with the English translation.

Hattori et al., "Theory of arrangement control of metallic nanoparticles by light fields with designed polarization distributions", The Japan Society of Applied Physics, pp. 01-163, Aug. 30, 2010.

International Search Report, mailed Mar. 13, 2012, issued in PCT/JP2011/078438.

Kalele et al., "Optical detection of antibody using silica-silver core-shell particles", Chemical Physics Letters, vol. 404, pp. 136-141, Mar. 7, 2005.

Sanchez-Gaytan et al., "Spiky Gold Nanoshells", Langmuir Article, vol. 26, No. 24, pp. 19170-19174, Nov. 19, 2010.

\* cited by examiner

CA (LONG AXIS: 30 nm    SHORT AXIS: 10 nm)

SILVER NANOPARTICLE FIXED BEAD

DEVICE AND METHOD UTILIZING A METALLIC NANOPARTICLE ASSEMBLY STRUCTURE FOR DETECTING A TARGET SUBSTANCE

TECHNICAL FIELD

The present invention relates to a device and method utilizing a metallic nanoparticle assembly structure for detecting a target substance.

BACKGROUND ART

In recent years, as an in-vitro diagnostic method, there has been proposed a diagnostic method utilizing presentation of color by localized surface plasmon resonance of colloidal gold. For example, in immunochromatography, there is proposed a method using colloidal gold having an antibody anchored thereto, as a tag-labeled particle. According to this method, when an antigen that is a target substance is contained in a specimen, the antigen and the tag-labeled particle are conjugated together to form a conjugate. The conjugate develops a moving bed and is captured by an antibody of a determination site. This causes the determination site to exhibit a red color. Whether the antigen is present or absent can be confirmed by confirming whether the determination site exhibits color.

For example, Japanese Patent Laying-Open No. 2009-210505 (PTD 1) discloses an immunological measurement kit aiming at application to immunochromatography. For example, Japanese National Patent Publication No. 2005-533246 (PTD 2) discloses a surface enhanced resonance Raman scattering (SERRS) active bead employed for identifying a target molecule. This bead includes aggregated metallic colloid and at least one SERRS active dye that are encapsulated in a polymer shell.

CITATION LIST

Patent Documents

PTD 1: Japanese Patent Laying-Open No. 2009-210505
PTD 2: Japanese National Patent Publication No. 2005-533246

SUMMARY OF INVENTION

Technical Problem

There constantly exists a need for a technique allowing a target substance to be detected with enhanced sensitivity, in other words, a technique allowing a trace amount of target substance to be detected. According to the method disclosed in Japanese Patent Laying-Open No. 2009-210505 (PTD 1), whether a determination site exhibits color can be confirmed to conveniently confirm whether an antigen is present or absent. It is believed, however, that visually confirming whether color is exhibited requires that a specimen should contain a target substance of a concentration of some high extent, and requires the target substance in a large amount.

An object of the present invention is to provide a device and method allowing a trace amount of a target substance to be detected to contribute to overcoming the above issue.

Solution to Problem

The present invention in one aspect provides a detection device for detecting a target substance that may be contained in a specimen. The detection device includes: a metallic nanoparticle assembly structure formed of metallic nanoparticles assembled together and modified with a first host molecule allowing the target substance to specifically adhere thereto; and a metallic nanostructure modified with a second host molecule allowing the target substance to specifically adhere thereto.

Preferably, the detection device further includes a substrate for fixing the metallic nanoparticle assembly structure thereto.

Preferably, the detection device further includes: a first light source for irradiating the specimen with light with the metallic nanoparticle assembly structure and the metallic nanostructure introduced in the specimen; a spectroscope for measuring a spectrum of the specimen; and a detector for detecting the target substance, based on the spectrum measured with the spectroscope.

Preferably, the first light source emits white light.

Preferably, the first light source emits substantially monochromatic light associated with one or a plurality of ranges corresponding to twice a full width at half maximum of a peak of localized surface plasmon resonance of at least one of the metallic nanoparticle assembly structure and the metallic nanostructure.

Preferably, the detection device further includes a second light source irradiating the specimen with polarized light.

Preferably, the spectrum measured with the spectroscope is an extinction spectrum of localized surface plasmon resonance. The extinction spectrum is a sum of a scattering spectrum and an absorption spectrum.

Preferably, the spectrum measured with the spectroscope is a surface enhanced Raman scattering (SERS) spectrum.

Preferably, the metallic nanoparticle assembly structure includes a bead having a surface with the metallic nanoparticles fixed thereto, and the metallic nanostructure is a metallic nanorod.

Preferably, the metallic nanorod has a short axis having a length equal to or larger than 1 nm, and when the metallic nanorod has an aspect ratio defined as a ratio of a long axis of the metallic nanorod to the length of the short axis, the aspect ratio has a value larger than 1.

Preferably, the metallic nanoparticle of the metallic nanoparticle assembly structure and the metallic nanorod are composed of metals, respectively, identical in type.

Preferably, the metallic nanoparticle of the metallic nanoparticle assembly structure and the metallic nanorod are composed of metals, respectively, different in type.

Preferably, the target substance is an antigen, and the first and second host molecules are an antibody causing an antigen-antibody reaction with the antigen.

The present invention in another aspect provides a method for detecting a target substance that may be contained in a specimen. The method includes the steps of: introducing a metallic nanoparticle assembly structure and a metallic nanostructure into the specimen, the metallic nanoparticle assembly structure being formed by assembling metallic nanoparticles together, the metallic nanoparticle being modified with a first host molecule allowing the target substance to specifically adhere thereto, the metallic nanostructure being modified with a second host molecule allowing the target substance to specifically adhere thereto. In addition, the method includes the step of irradiating the specimen with light; measuring a spectrum of the specimen; and detecting the target substance, based on the spectrum.

Preferably, the step of irradiating the specimen with light includes the step of irradiating the specimen with polarized light to collect the metallic nanoparticle assembly structure and the metallic nanostructure.

Preferably, the step of irradiating the specimen with light includes the step of irradiating the specimen with white light.

Preferably, the step of exposing the specimen to light includes the step of irradiating the specimen with substantially monochromatic light associated with one or a plurality of ranges corresponding to twice a full width at half maximum of a peak of localized surface plasmon resonance of at least one of the metallic nanoparticle assembly structure and the metallic nanostructure.

Preferably, the spectrum is an extinction spectrum of localized surface plasmon resonance.

Preferably, the spectrum is a surface enhanced Raman scattering (SERS) spectrum.

The present invention in still another aspect provides a method for detecting a target substance, causing a target substance to specifically adhere to a bead having a surface with metallic nanoparticles fixed thereto, to measure an extinction spectrum of localized surface plasmon resonance.

The present invention in still another aspect provides a method for detecting a target substance, causing a target substance to specifically adhere to a bead having a surface with metallic nanoparticles fixed thereto, to measure a surface enhanced Raman scattering (SERS) spectrum.

Advantageous Effects of Invention

The present invention can thus provide a device and method allowing a trace amount of a target substance to be detected.

DESCRIPTION OF EMBODIMENTS

Figure 1:
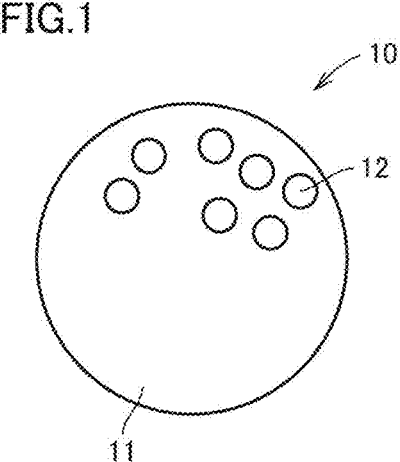
FIG. 1 schematically shows a metallic nanoparticle assembly structure used in an embodiment of the present invention.

Hereinafter, an embodiment of the present invention will specifically be described with reference to the drawings. In the figures, identical or corresponding components are identically denoted and will not be described repeatedly in detail.

In the present invention and its embodiment(s), a "metallic nanoparticle assembly structure" is a structure formed by assembling a plurality of metallic nanoparticles. A "metallic nanoparticle" is a metallic particle having a size on an order of nanometers. An "order of nanometers" includes a range of one to several hundreds nanometers and typically it ranges from 1 to 100 nm, preferably from 1 to 50 nm.

In the present invention and its embodiment(s), a "metallic nanostructure" is a metallic structure having a size on an order of nanometers. A structure formed by assembling metallic nanoparticles can also be included in the metallic nanostructure.

In the present invention and its embodiment(s), a "host molecule" is a molecule allowing a target substance to specifically adhere thereto. Combinations of the host molecule allowing a target substance to specifically adhere thereto and the target substance include for example: antigen and antibody; sugar chain and protein; lipid and protein; a low molecule compound (ligand) and protein; protein and protein; single stranded DNA and single stranded DNA; and the like. When such a specifically affinitive combination has one component corresponding to a target substance, the other component can be used as a host molecule. In other words, if an antigen is a target substance, an antibody can be used as a host molecule. On the contrary, if an antibody is a target substance, an antigen can be used as a host molecule. Furthermore, in hybridization of DNA, a target substance is an analyte DNA, and a host molecule is a probe DNA. Furthermore, an "antigen" can include allergen and virus. Furthermore, the present invention and its embodiment(s) also allow an antibody to be changed in type to change a type of allergen or virus detectable. The present invention and its embodiment(s) thus do not limit detectable allergen or virus in type.

Furthermore in the present invention and its embodiment(s) a target substance may be an organic molecule that is not limited to a biomolecule.

Furthermore in the present invention and its embodiment(s) a target substance may be a heavy metal ion. In that case, a molecule capable of capturing the heavy metal ion can be utilized as a host molecule.

A "first host molecule" and a "second host molecule" are host molecules that can specifically adhere to a target substance at different sites. For example, if an antigen is a target substance, the first host molecule is a primary antibody and the second host molecule is a secondary antibody.

In the present invention and its embodiment(s) the term "white light" means continuous or pulsed light having a range in wavelength of a visible range-including ultraviolet to near-infrared range (e.g., a range in wavelength of 200 nm to 1100 nm).

In the present invention and its embodiment(s) the term "monochromatic light" is light having a wavelength in a range corresponding to twice a full width at half maximum of a peak of localized surface plasmon resonance of at least one of a metallic nanoparticle assembly structure and a metallic nanostructure. The number of ranges corresponding to twice a full width at half maximum of a peak of localized surface plasmon resonance may be one or plural.

In the present invention and its embodiment(s) the term "polarization" means an electric field vector perpendicular to a direction in which an optical electromagnetic wave propagates.

In the present invention and its embodiment(s), a "specimen" means a substance that may include a substance including a target substance or the target substance. The specimen may be biological specimens obtained for example from animals (e.g., human, cow, horse, pig, goat, chicken, rat, mouse, and the like). The biological specimen may include blood, tissues, cells, bodily secretions, body fluids, and the like, for example. Note that the "specimen" may also include its dilutions.

In the present invention and its embodiment(s), a "medium" means an environment in which the metallic nanoparticle assembly structure exists.

<Metallic Nanoparticle Assembly Structure>

Figure 2:
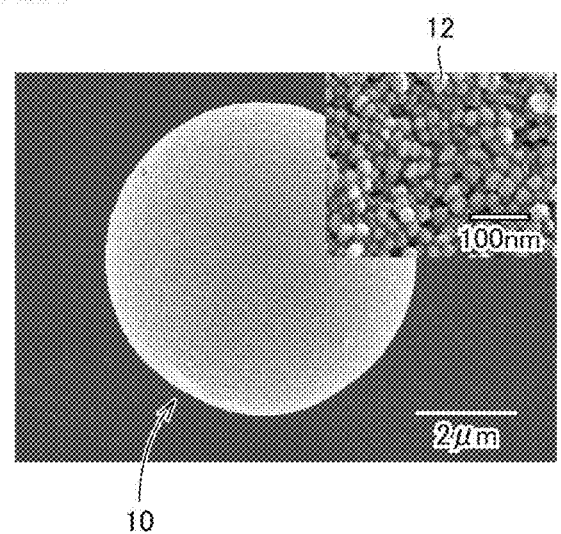
FIG. 2 is an image of a metallic nanoparticle assembly structure of one example obtained with a scanning electron microscope (SEM).

FIG. 1 schematically shows a metallic nanoparticle assembly structure used in an embodiment of the present invention. FIG. 2 is an image of a metallic nanoparticle assembly structure of one example obtained with a scanning electron microscope (SEM).

With reference to FIG. 1 and FIG. 2, metallic nanoparticle assembly structure 10 has a bead 11 and metallic nanoparticles 12. Metallic nanoparticle 12 covers a surface of bead 11 and is also fixed to the surface of bead 11. Thus a structure of an assembly of metallic nanoparticles 12 is formed.

The bead has an average diameter on a submicron order or a micron order, e.g., 0.1-100 μm, more preferably 0.1-10 μm.

Bead 11 is a resin particle. Bead 11 may be formed of any material that is capable of forming a particle having a diameter as desired. Bead 11 is formed for example of, but not limited to, acryl, polyolefin, polyethylene, polypropylene, polystyrene and/or similar resin.

The resin can be made into a fine particle in any method that can be employed in the field of the art, for example by monomer casting, suspension polymerization, melt spin coating, ultracentrifugation, ultrasonic wave or the like selected as appropriate depending on the type of the resin.

The metallic nanoparticle is a metallic nanoparticle that can cause localized surface plasmon resonance. The metallic nanoparticle is a gold nanoparticle for example. As will be described more specifically, when the gold nanoparticle is irradiated with light of the visible to near-infrared ranges, localized surface plasmon resonance is induced on a surface of the gold nanoparticle. Any metallic nanoparticle other than the gold nanoparticle that can cause localized surface plasmon resonance is applicable to the present invention. Another such exemplary metallic nanoparticle is a silver nanoparticle, for example. In this embodiment, these gold and silver nanoparticles are adopted.

The metallic nanoparticle has an average diameter on a subnanometer order to a nanometer order (approximately 2 nm to 1000 nm), and it can for example be 2-500 nm, preferably 2-100 nm, more preferably 5-50 nm.

The metallic nanoparticle can be fixed to a surface of bead 11 via a site that can interact with the metallic nanoparticle that exists on the surface of bead 11. The "interaction" refers to chemical bonding, Van der Waals force, electrostatic interaction, hydrophobic interaction, adsorption power, and the like. If the metallic nanoparticle is a gold nanoparticle, then, a site (or group) that can interact with gold is, but not limited to, thiol group, for example. The interacting site may previously be provided on a surface of bead 11, or may previously be provided on a surface of colloidal gold, for example.

The metallic nanoparticle can be fixed to a surface of a bead in a variety of known methods. For example, when a gold nanoparticle is fixed to a surface of a bead, the bead may be mixed in a gold nanoparticle dispersion liquid, which may in turn be agitated or placed still. The gold nanoparticle dispersion liquid may optionally contain an organic binder. The fixing reaction temperature can be any temperature that does not cause the dispersion liquid to completely freeze or evaporate during the period of the reaction. Preferably, the fixing reaction temperature is room temperature (for example of 10-35° C.).

The gold nanoparticle dispersion liquid may be a commercially available product or may be produced by using a gold ion (or gold complex ion) containing solution and a reducing agent and thereby conducting a reductive reaction in the solution. For example, a chlorauric acid solution with citric acid added thereto may be used.

Preferably, the metallic nanoparticle assembly structure is fixed on a substrate. However, the metallic nanoparticle assembly structure may be dispersed in a medium (e.g., in a liquid).

Figure 3:
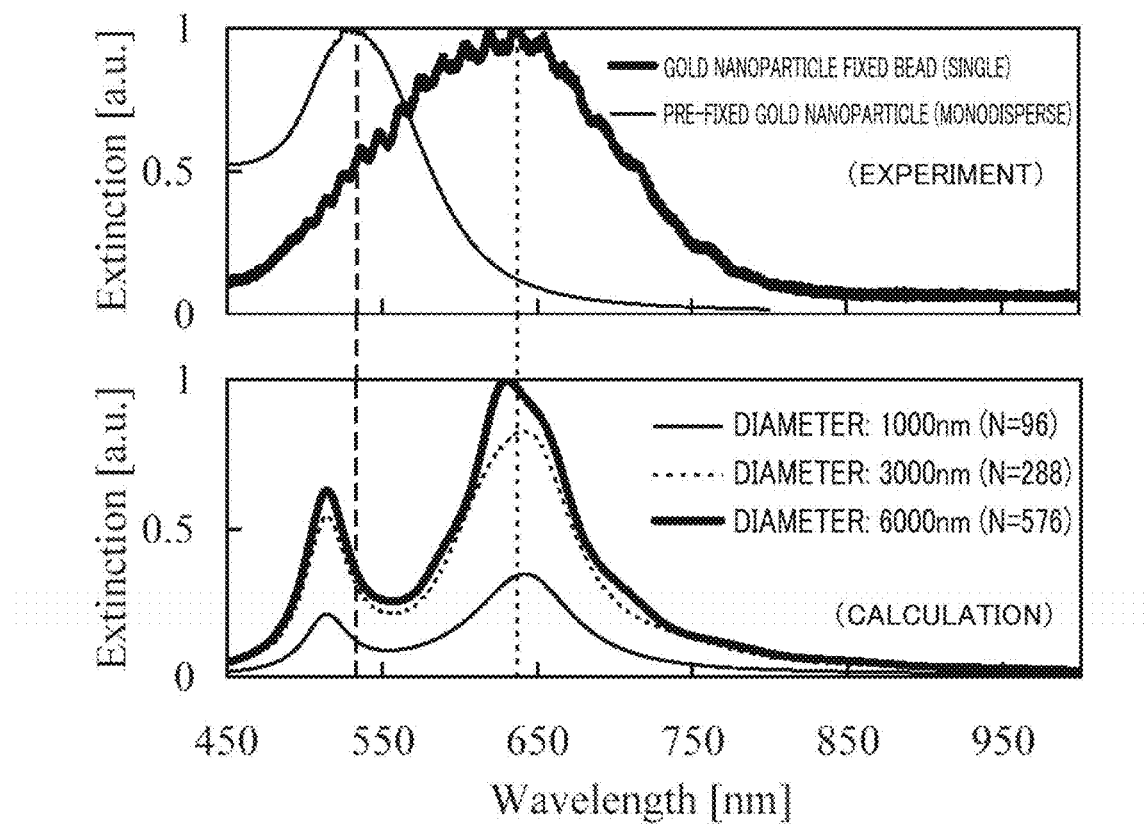
FIG. 3 shows a measurement result of an extinction spectrum of a metallic nanoparticle assembly structure 10 according to an embodiment of the present invention and a calculation result of an extinction spectrum of localized surface plasmon resonance.

FIG. 3 shows a measurement result of an extinction spectrum of metallic nanoparticle assembly structure 10 according to an embodiment of the present invention and a calculation result of an extinction spectrum of localized surface plasmon resonance.

With reference to FIG. 3, a graph indicated as "experiment" shows a measurement result of an extinction spectrum of the metallic nanoparticle assembly structure. This measurement result is based on localized surface plasmon resonance induced at a gold nanoparticle fixed to a bead of 6 μm in diameter. As shown in this graph, the extinction spectrum peaks at a wavelength of approximately 650 nm.

Figure 4:
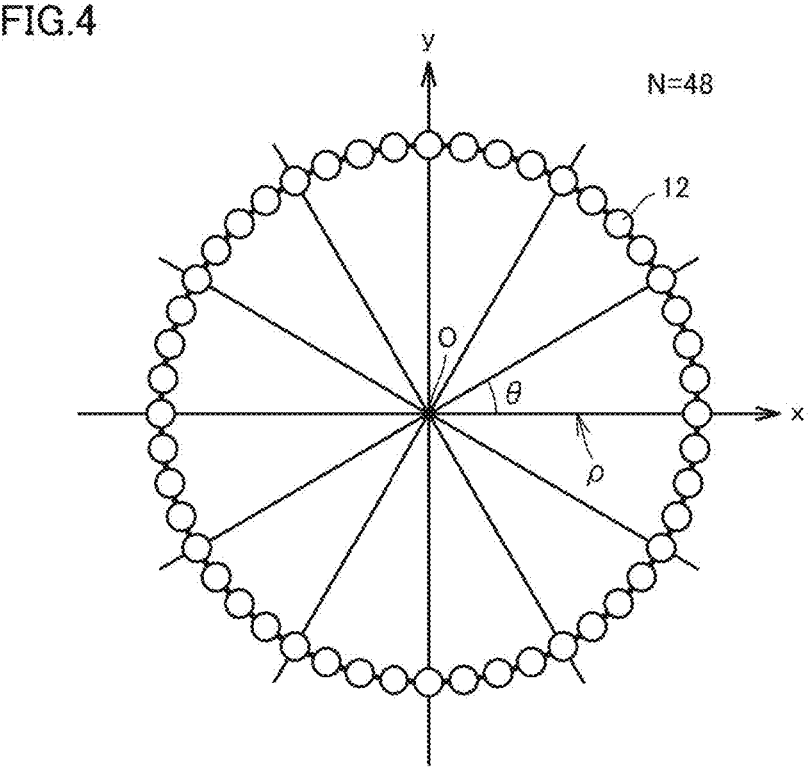
FIG. 4 shows a two-dimensional model for calculating extinction, scattering, and absorption spectra of localized surface plasmon resonance.

A graph indicated as "calculation" shows calculation results of extinction and absorption spectra of localized surface plasmon resonance. FIG. 4 shows a two-dimensional model for calculating extinction, scattering, and absorption spectra of localized surface plasmon resonance.

With reference to FIG. 4, N particles arranged in a ring structure on a plane were used for a calculation model. ρ represents a radius of a circle formed by arranging the N particles in the ring structure, and corresponds to a radius of bead 11.

In the calculation model, the metallic nanoparticle had a diameter set to 30 nm and any two adjacent metallic nanoparticles had their respective centers with a distance of 32.7 nm therebetween. Although FIG. 4 shows a model with N=48 set as an example, models with N=96, N=288 and N=576 were used to calculate extinction and absorption spectra. N=96 provides a circle having radius ρ of 500 nm. N=288 provides a circle having radius ρ of 1500 nm. N=576 provides a circle having radius ρ of 3000 nm.

Extinction and absorption spectra of localized surface plasmon resonance can be calculated by using this calculation model to solve a Maxwell equation as a discretized integral equation. Light absorption ($C_{abs}$) is represented by a current J, an electric field E, and a susceptibility $\chi$ according to the following equation (1):

$$C_{abs} = \langle J \cdot E \rangle = \frac{\omega}{2} \text{Im}[\chi]|E|^2. \tag{1}$$

Extinction spectrum is converted from dissipative force in a direction in which light applied to the entire system propagates. This dissipative force is proportional to light scattering and absorption (T. Iida, H. Ishihara, "Nano-Optical Manipulation Using Resonant Radiation Force" Progress in Nano-Electro-Optics VI, edited by M. Ohtsu, Springer, Berlin 2008).

Figure 5:
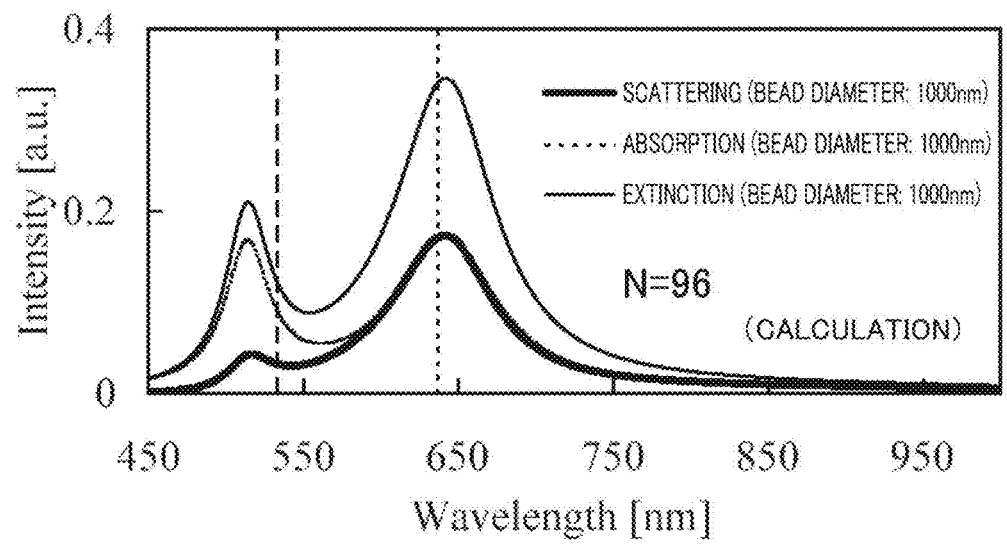
FIG. 5 shows calculation results of extinction, scattering and absorption spectra of localized surface plasmon resonance when the FIG. 4 two-dimensional model has a number N of particles set to 96.
Figure 6:
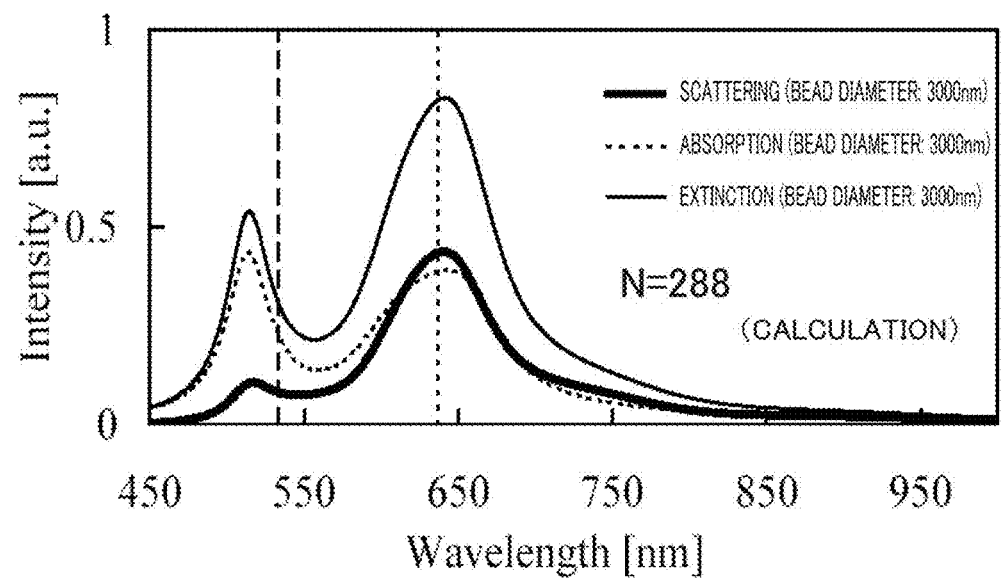
FIG. 6 shows calculation results of extinction, scattering and absorption spectra of localized surface plasmon resonance when the FIG. 4 two-dimensional model has a number N of particles set to 288.
Figure 7:
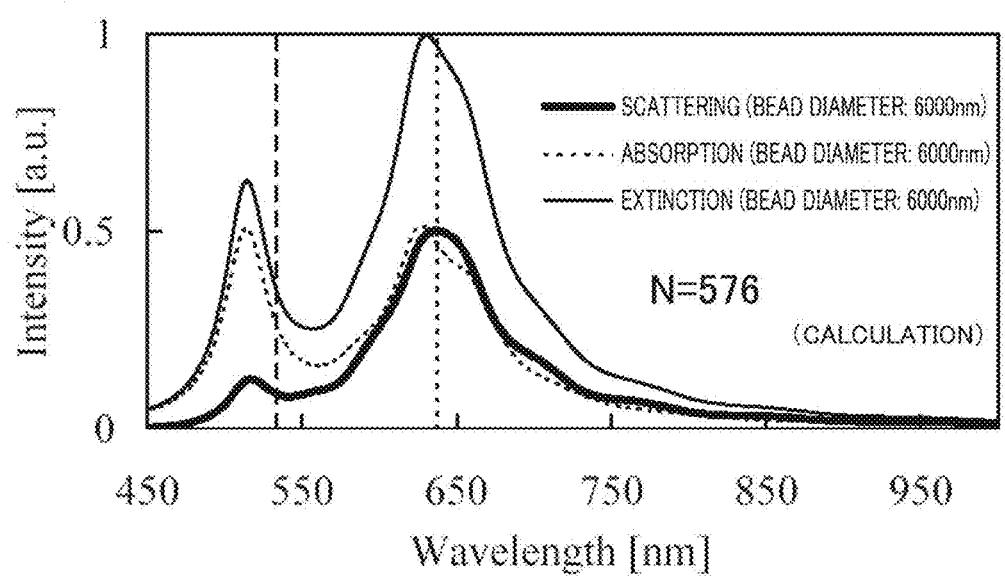
FIG. 7 shows calculation results of extinction, scattering and absorption spectra of localized surface plasmon resonance when the FIG. 4 two-dimensional model has a number N of particles set to 576.

FIG. 5 shows calculation results of extinction, scattering and absorption spectra of localized surface plasmon resonance when the FIG. 4 two-dimensional model has a number N of particles set to 96. FIG. 6 shows calculation results of extinction, scattering and absorption spectra of localized surface plasmon resonance when the FIG. 4 two-dimensional model has a number N of particles set to 288. FIG. 7 shows calculation results of extinction, scattering and absorption spectra of localized surface plasmon resonance when the FIG. 4 two-dimensional model has a number N of particles set to 576.

With reference to FIG. 5 to FIG. 7, it can be seen that the extinction, absorption and scattering spectra have their respective peaks positionally substantially unvarying while the bead varies in diameter. Accordingly, any of the extinction, absorption and scattering spectra may be detected. Note that the scattering spectra shown in FIG. 5 to FIG. 7 are calculated according to the relationship of (extinction)=(absorption)+(scattering).

As can also be seen from the calculation results of FIG. 3 and FIG. 5 to FIG. 7, localized surface plasmon presents extinction, scattering and absorption spectra having substantially identical spectral peak positions, and accordingly in the present invention any of the extinction, scattering and absorption spectra may be detected.

It is assumed that the metallic nanoparticle is a spherical cell. A response optical electric field can be described with an integral form of a Maxwell equation. An electric field $E_i$ is represented according to the following equation (2):

$$E_i = E_i^0 + \sum_{j=1, j \neq i}^{N_p} G_{r,r',\omega}(i-j) \cdot P_j V_j + M_i \cdot P_i - \frac{L \cdot P_i}{k^2}, \tag{2}$$

where i and j represent particle numbers of spherical cells, and M and L represent amounts associated with self-interaction.

Susceptibility and electric field distributions in individual metallic structures are assumed to be flat. Induced polarization $P_i$ is represented according to the following equation (3) (O. J. F. Martin, N. B. Piller, and Phys. Rev. E 58 3909 (1998)):

$$P_i = \chi_i(\omega) E_i \tag{3}.$$

Susceptibility and electric field distributions in individual spherical metallic nanoparticles are assumed to be flat. Equations (2) and (3) are simultaneously and numerically solved as self-consistent equations to obtain a response optical electric field and induced polarization, and as a function thereof are obtained extinction, scattering, and absorption spectra of localized surface plasmon resonance. Note that a Drude model is applied to susceptibility $\chi$. Susceptibility $\chi$ is represented according to the following equation (4):

$$\chi = \chi_b - \frac{\omega_p^2}{\omega^2 + i\omega(\gamma + V_f/a)}, \quad (4)$$

where $\chi_b$ represents susceptibility of a background (a non-resonant portion), $\omega_p$ represents plasma energy, $\gamma$ represents a nonradiative relaxation constant, and $V_f$ represents electron velocity on the Fermi surface. The nonradiative relaxation constant is a value indicative of relaxation from an excited electron to other than light (e.g., heat). Furthermore, a represents a radius of the particle.

For the calculation, bead 11 and the surrounding medium had an index of refraction close to that of water, i.e., 1.33. Furthermore, the non-resonant portion had a relative dielectric constant set to 11. Plasma energy $\omega_p$ was set to 8.958 (eV). Nonradiative relaxation rate $\gamma$ was set to 72.3 (meV). Electron velocity $V_f$ on the Fermi surface was set to 0.922 (nm-eV). The particle had radius a set to 30 (nm).

Returning to FIG. 3 and FIG. 5 to FIG. 7, for any of N=96, N=288 and N=576, the graphs indicated as "calculation" present absorption and extinction spectra having a peak wavelength of approximately 650 nm. This indicates that a result based on the above theory and calculation sufficiently reproduces an experimental result.

Furthermore, it can be seen from this calculation result that when the particles have a fixed interparticle distance, the extinction and absorption spectra both have a peak wavelength substantially unvarying while bead 11 varies in diameter (or metallic nanoparticle assembly structure 10 varies in size). On the other hand, as will be described hereinafter, smaller interparticle distance (or higher particle density) results in larger shift toward a longer wavelength range, whereas larger interparticle distance results in smaller shift toward the longer wavelength range.

Note that while the calculation result indicates that the extinction and absorption spectra peak not only around a wavelength of 650 nm but also around a wavelength of 500 nm, the experimental result does not indicate the extinction spectrum with a peak around a wavelength of 500 nm. It is presumed that this is because gold nanoparticles are fixed at different interparticle distances and the extinction spectrum accordingly has overlapping peaks for different wavelengths from around 500 nm to around 650 nm.

Figure 8:
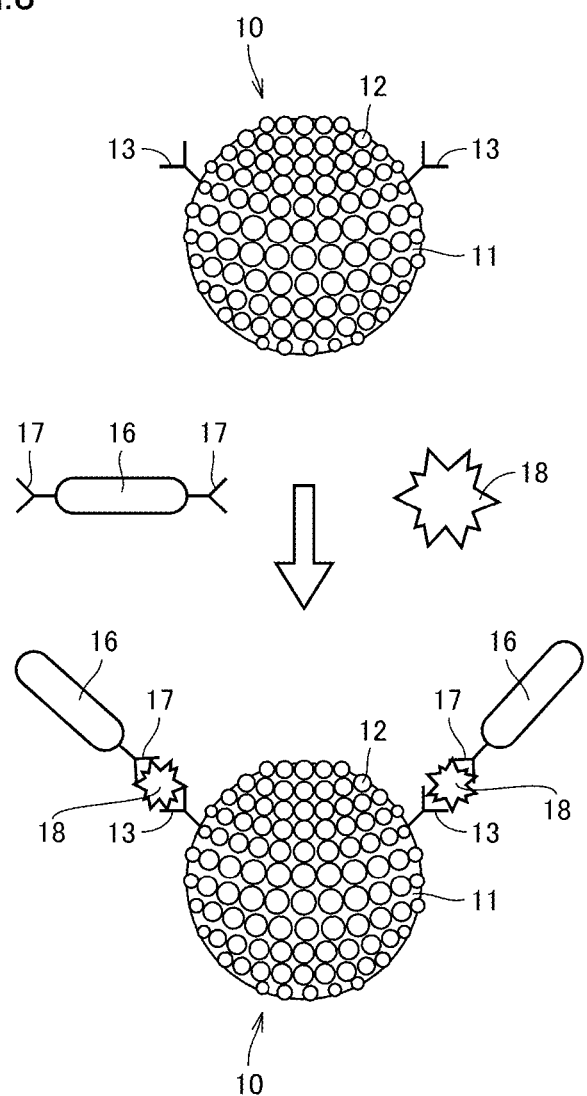
FIG. 8 schematically illustrates a method for detecting a target substance according to an embodiment of the present invention.

FIG. 8 schematically illustrates a method for detecting a target substance according to an embodiment of the present invention. With reference to FIG. 8, in the present embodiment, metallic nanoparticle assembly structure 10 modified with a host molecule 13 and a metallic nanorod 16 modified with a host molecule 17 are used to detect a target substance 18. Metallic nanorod 16 corresponds to a metallic nanostructure. For the sake of illustration, FIG. 8 shows some metallic nanoparticles 12 modified with host molecule 13 and metallic nanorod 16 partially modified with host molecule 17. However, host molecule 13 may modify the entire surface of metallic nanoparticle assembly structure 10, and host molecule 17 may also similarly modify the entire surface of metallic nanorod 16.

Target substance 18 is a virus or DNA, for example. Host molecule 13 is a primary antibody and host molecule 17 is a secondary antibody. Metallic nanoparticle assembly structure 10 and metallic nanorod 16 are conjugated by a reaction between a virus and an antibody. This results in a varied extinction spectrum. Accordingly, target substance 18 can be detected by measuring the extinction spectrum.

As set forth above, host molecule 13 and host molecule 17 are conjugated via target substance 18. According to this embodiment, appropriately selecting host molecules 13 and 17 allows various substances to be detected. In one example, target substance 18 is an organic molecule that is not limited to a biomolecule. In another example, target substance 18 is a heavy metal ion, and host molecules 13 and 17 are each for example a complex molecule or a similar a molecule capable of capturing the heavy metal ion.

Note that, in the following description, metallic nanoparticle assembly structure 10 and metallic nanorod 16 conjugated by target substance 18 will be referred to as a "metallic nanorod conjugate" for the sake of convenience.

Figure 9:
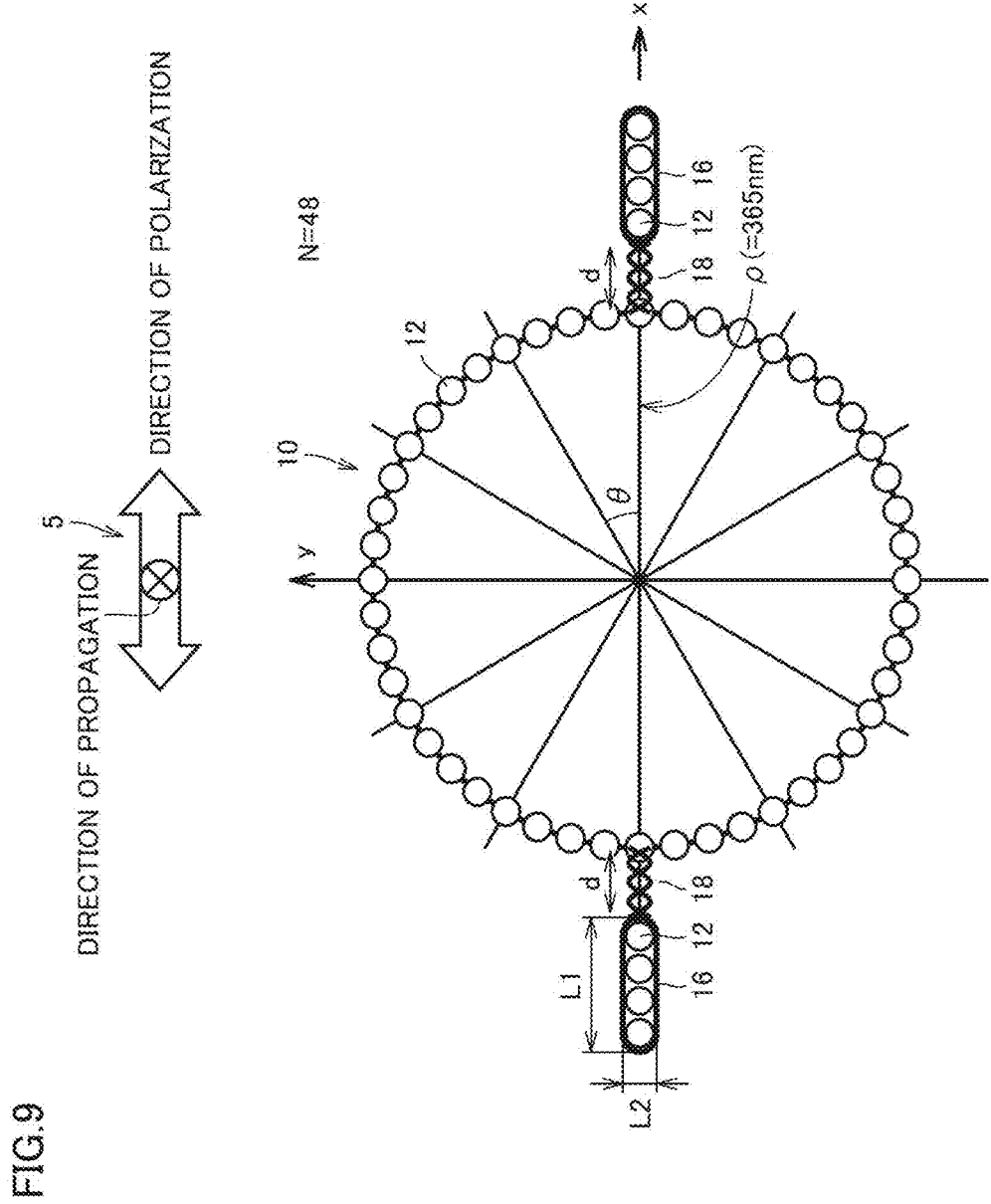
FIG. 9 shows a two-dimensional model for calculating an extinction spectrum of a metallic nanorod conjugate.

FIG. 9 shows a two-dimensional model for calculating an extinction spectrum of a metallic nanorod conjugate. With reference to FIG. 9, metallic nanorod 16 is represented as a plurality of metallic nanoparticles 12 arranged in one direction. Metallic nanorod 16 along its long and short axes has lengths L1 and L2, respectively.

Metallic nanorod 16 has an aspect ratio defined as a ratio of length L1 of metallic nanorod 16 along its long axis to length L2 of metallic nanorod 16 along its short axis. L1 is larger than L2, and accordingly, the aspect ratio (L1/L2) is larger than one.

Metallic nanorod 16 is conjugated to metallic nanoparticle assembly structure 10 by target substance 18 (e.g., a virus or DNA). In this condition, metallic nanorod 16 has its long and short axes in the x- and y-directions, respectively, for the sake of illustration. d represents a distance between metallic nanoparticle assembly structure 10 and metallic nanorod 16.

This model was used to calculate an extinction spectrum. The extinction spectrum was calculated with metallic nanoparticle 12 implemented as a gold nanoparticle each having a diameter of 30 nm. Metallic nanoparticle assembly structure 10 was formed with number N of metallic nanoparticles 12 (gold nanoparticles) set to 48. Metallic nanoparticle assembly structure 10 had radius $\rho$ set to 365 nm. In that case, metallic nanoparticle assembly structure 10 has any two adjacent metallic nanoparticles 12 having a center-to-center distance of 47.8 nm and a minimum surface-to-surface distance of 17.8 nm.

Metallic nanorod 16 was formed of four metallic nanoparticles 12 (gold nanoparticles). Accordingly L1 is 120 nm and L2 is 30 nm. Furthermore, d was set to 2 nm. Furthermore, polarized light 5 is polarized in the x-direction, and polarized light 5 propagates in a direction perpendicular to the plane of the sheet of the drawing.

Figure 10:
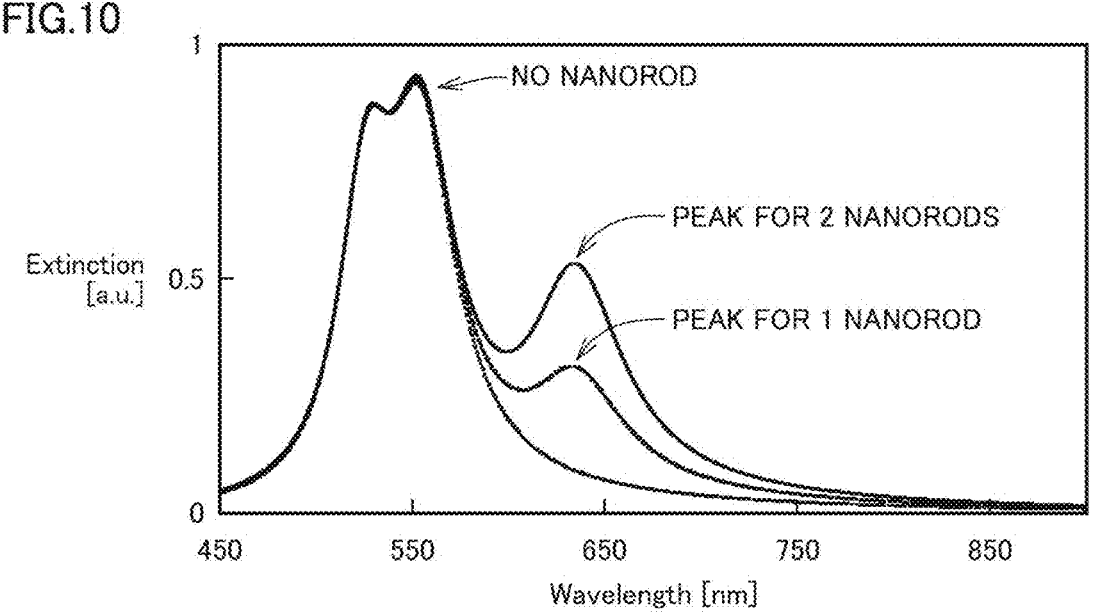
FIG. 10 shows a calculation result of an extinction spectrum by using the model of the metallic nanorod conjugate shown in FIG. 9.

FIG. 10 shows a calculation result of an extinction spectrum by using the model of the metallic nanorod conjugate shown in FIG. 9. With reference to FIG. 9 and FIG. 10, if there is no metallic nanorod 16, i.e., if no metallic nanorod is conjugated to metallic nanoparticle assembly structure 10, the extinction spectrum peaks only around a wavelength of 550 nm. It peaks at a position different than FIG. 3 because of a different inter-particle distance as set forth above. In contrast, when metallic nanorod 16 is conjugated to metallic nanoparticle assembly structure 10, the extinction spectrum peaks not only around a wavelength of 550 nm but also around a wavelength of 650 nm. The peak around the wavelength of 650 nm is a spectral component corresponding to a long-axis mode of the metallic nanorod conjugate, that is caused as the metallic nanorod is conjugated to metallic nanoparticle assembly structure 10.

When metallic nanoparticle assembly structure 10 had one metallic nanorod conjugated thereto, the ratio of the peak at the wavelength of 550 nm and that at the wavelength of 650 nm was estimated as approximately 3:1 as a peak intensity ratio (or a signal intensity ratio). A ratio of the metallic nanoparticle assembly structure in total in volume to a single metallic nanorod in volume is approximately 12:1. It was confirmed that as the number of metallic nanorods conjugated to metallic nanoparticle assembly structure 10 was increased from one to two, the peak around approximately 650 nm became larger.

In other words, the FIG. 10 result indicates that target substance 18 can be detected by detecting in the extinction spectrum a peak corresponding to the long-axis mode of the metallic nanorod conjugate (in the FIG. 10 example, the peak around the wavelength of 650 nm). Furthermore, it also represents that the peak has a magnitude depending on the number of the metallic nanorods conjugated to metallic nanoparticle assembly structure 10. The number of metallic nanorods conjugated to metallic nanoparticle assembly structure 10 depends on an amount of a target substance contained in a specimen. Accordingly, when a specimen contains a target substance at larger concentration, a peak corresponding to the long-axis mode of the metallic nanorod conjugate increases in magnitude.

It is desired, however, that a target substance be detected with higher sensitivity. Accordingly in the present embodiment preferably metallic nanoparticle assembly structure 10 is reduced in size. When metallic nanoparticles are fixed to a smaller bead, the bead will have a smaller number of metallic nanoparticles fixed thereto. Accordingly, even with only a small number of (e.g., one or two) metallic nanorods conjugated to metallic nanoparticle assembly structure 10, a peak of an extinction spectrum caused by the metallic nanorod's own localized surface plasmon can clearly be measured. In other words, a trace amount of a target substance can be detected. This point will be described in detail hereinafter.

Figure 11:
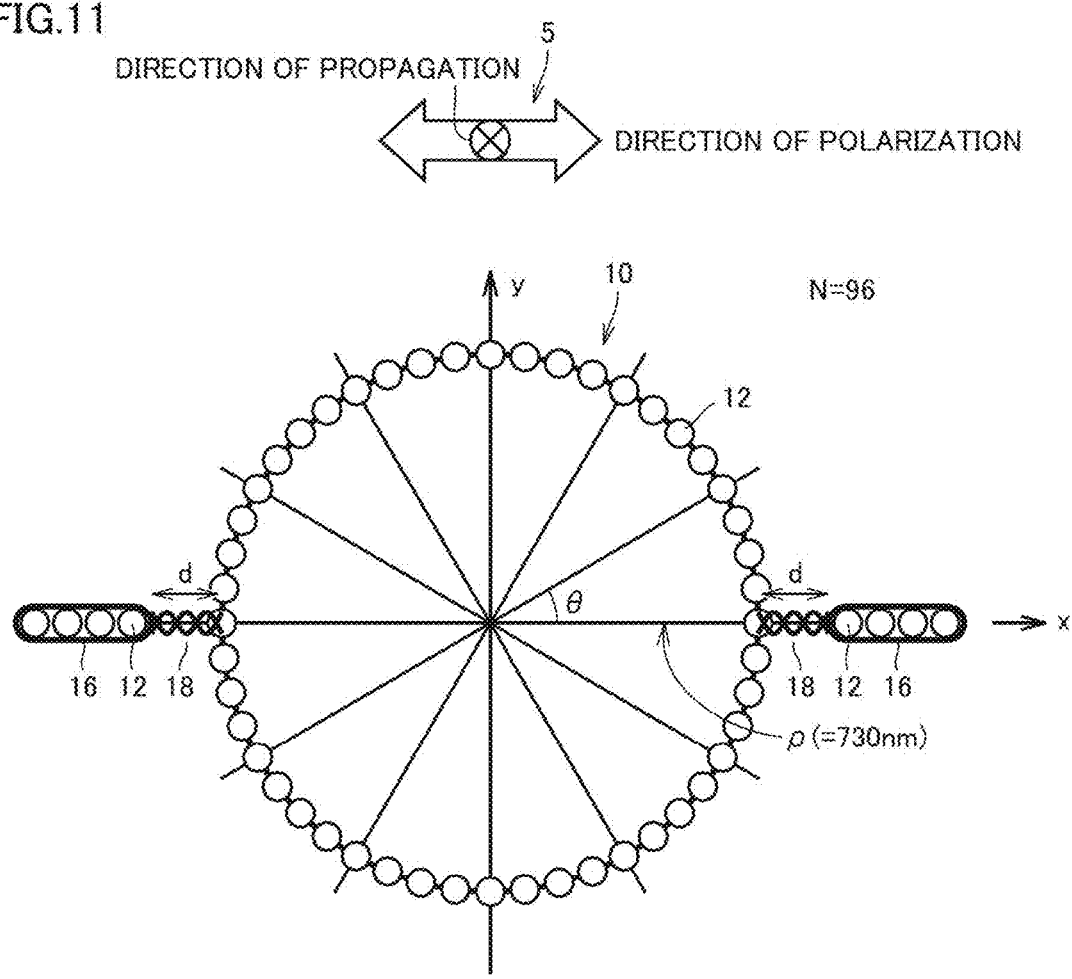
FIG. 11 shows a calculation model when metallic nanoparticle assembly structure 10 has a large size.

FIG. 11 shows a calculation model when metallic nanoparticle assembly structure 10 has a large size. With reference to FIG. 11, number N of metallic nanoparticles 12 configuring metallic nanoparticle assembly structure 10 was set to 96, and radius ρ of metallic nanoparticle assembly structure 10 was set to 730 nm. The FIG. 11 two-dimensional model and the FIG. 9 two-dimensional model have metallic nanoparticles 12 equal in density (or inter-particle distance). As well as in FIG. 9, polarized light 5 is polarized in the x-direction, and polarized light 5 propagates in a direction perpendicular to the plane of the sheet of the drawing.

Figure 12:
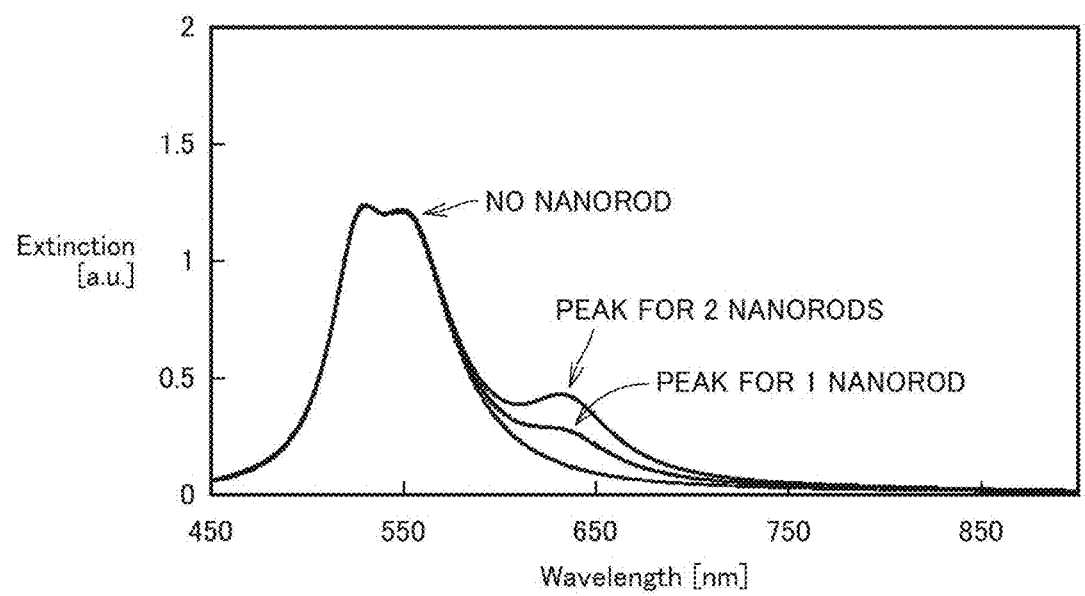
FIG. 12 shows a calculation result of an extinction spectrum by using a model of a metallic nanorod conjugate shown in FIG. 11.

FIG. 12 shows a calculation result of an extinction spectrum by using the model of the metallic nanorod conjugate shown in FIG. 11. With reference to FIG. 10 and FIG. 12, when metallic nanoparticle assembly structure 10 is increased in size, a ratio of a peak at the wavelength of 650 nm to that at the wavelength of 550 nm will decrease. From the result indicated in FIG. 12, when a single metallic nanorod conjugates to a metallic nanoparticle assembly structure, a signal intensity ratio of approximately 4.4:1 is presented. A ratio of the metallic nanoparticle assembly structure in total in volume to a single metallic nanorod in volume is approximately 24:1.

From the FIGS. 10 and 12 results, it can be seen that metallic nanoparticle assembly structure 10 small in size allows more efficient detection.

Figure 13:
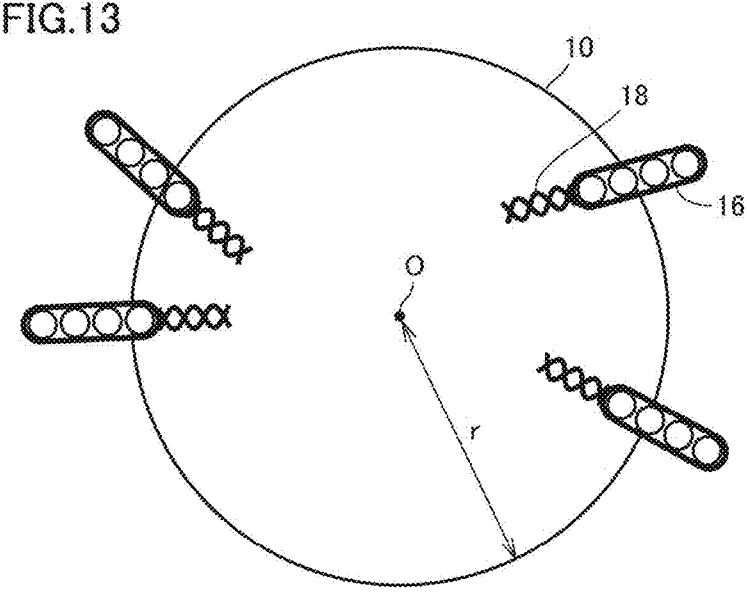
FIG. 13 schematically shows the condition in which a metallic nanoparticle assembly structure having a relatively large radius with metallic nanorods conjugated thereto.
Figure 14:
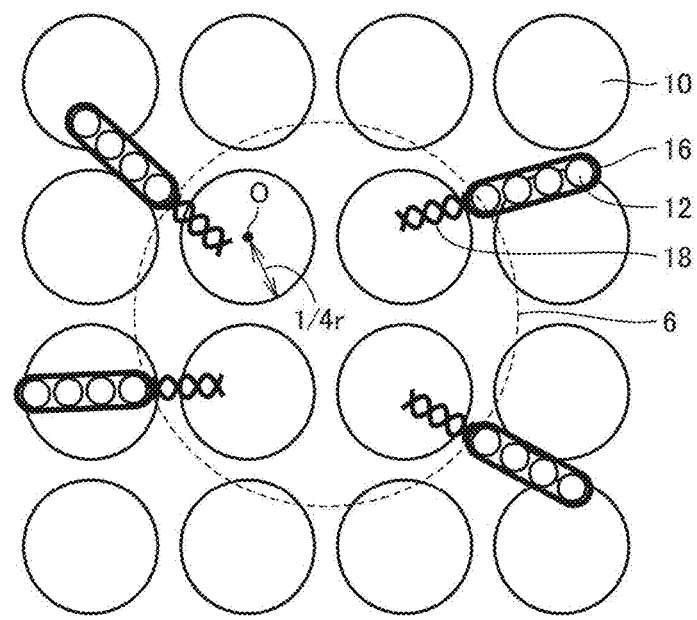
FIG. 14 schematically shows a metallic nanoparticle assembly structure having a relatively small radius (or a bead) with metallic nanorods conjugated thereto.

FIG. 13 schematically shows a metallic nanoparticle assembly structure having a relatively large radius with metallic nanorods conjugated thereto. FIG. 14 schematically shows a metallic nanoparticle assembly structure having a relatively small radius (or a bead) with metallic nanorods conjugated thereto.

The FIG. 13 example shows four metallic nanorods 16 conjugated to a single metallic nanoparticle assembly structure 10. Metallic nanoparticle assembly structure 10 is assumed to be a sphere with a radius r (for example of 4 μm). Metallic nanoparticle assembly structure 10 has a surface area of $4\pi r^2$ and a volume of $(4/3)\pi r^3$.

The FIG. 14 example shows 16 metallic nanoparticle assembly structures 10 disposed in four rows and four columns. Each metallic nanoparticle assembly structure 10 has a radius of r/4 (1 μm). Four (2×2) metallic nanoparticle assembly structures 10 positioned at a center each have a single metallic nanorod 16 conjugated thereto. 16 metallic nanoparticle assembly structures 10 together provide a total surface area of $16 \times 4\pi \times (r/4)^2 = 4\pi r^2$, which is equal to the surface area of metallic nanoparticle assembly structure 10 shown in FIG. 11. In contrast, 16 metallic nanoparticle assembly structures 10 together provide a total volume of $16 \times (4/3)\pi \times (r/4)^3 = 1/3\pi r^3$, which is equal to one fourth of the volume of metallic nanoparticle assembly structure 10 shown in FIG. 13.

As shown in FIG. 13 and FIG. 14, metallic nanoparticle assembly structures 10 small in size that are densely arranged can present a reduced volume while maintaining an area to which a metallic nanorod is fixed. This can contribute to a reduced cost for materials.

Furthermore, as shown in FIG. 14, a detection light spot 6 covers the region of four metallic nanoparticle assembly structures 10 having metallic nanorods conjugated thereto. For a given density of metallic nanoparticles, metallic nanoparticle assembly structure 10 larger in size results in an extinction spectrum having a peak dominated by metallic nanoparticle assembly structure 10. This makes a peak that is attributed to a metallic nanorod less observable for a given number of metallic nanorods conjugated to metallic nanoparticle assembly structure 10 (see FIG. 12). For a given size of spot 6, metallic nanoparticle assembly structure 10 reduced in size allows a spectral peak that is attributed to a metallic nanorod to be clearly confirmed.

Figure 15:
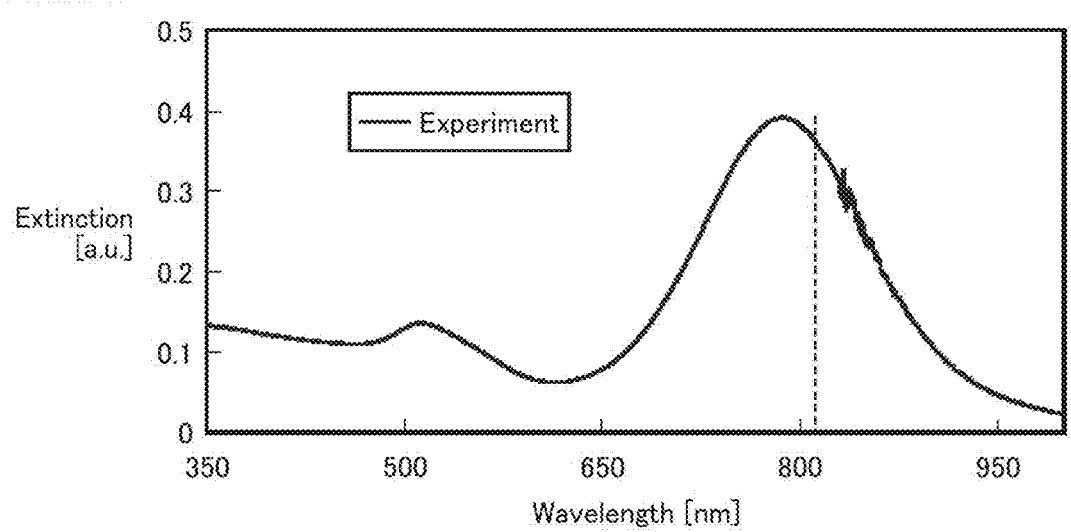
FIG. 15 shows a measurement result of an extinction spectrum of a gold nanorod.
Figure 16:
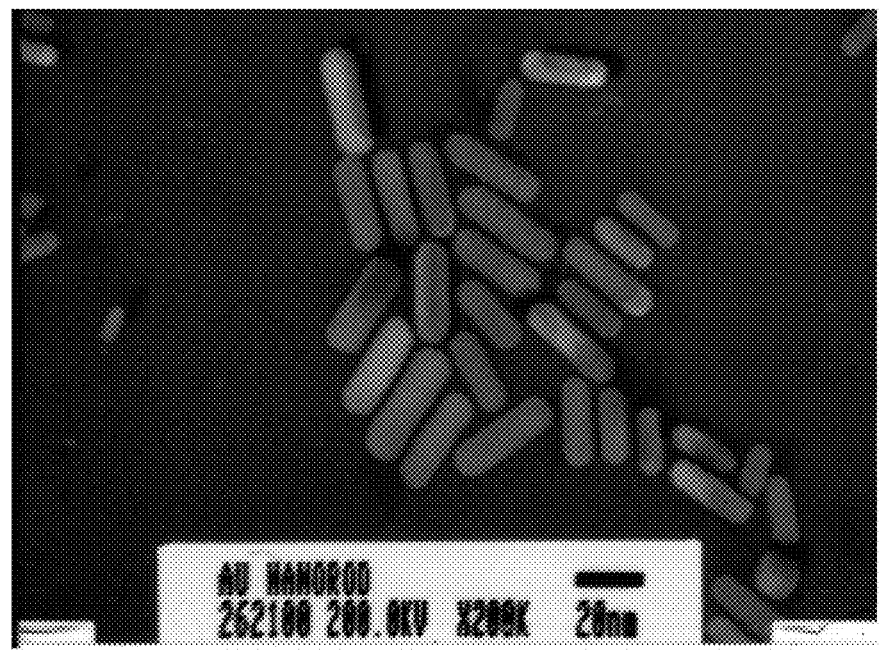
FIG. 16 is an image via a transmission electron microscope (TEM) of the gold nanorod used in measuring the extinction spectrum.

FIG. 15 shows a measurement result of an extinction spectrum of a gold nanorod. FIG. 16 is an image via a transmission electron microscope (TEM) of the gold nanorod used in measuring the extinction spectrum. With reference to FIG. 15 and FIG. 16, it was estimated from the TEM image that the gold nanorod had a long axis of approximately 30 nm in length and a short axis of approximately 10 nm in length. The extinction spectrum peaks at approximately 800 nm.

Figure 17:
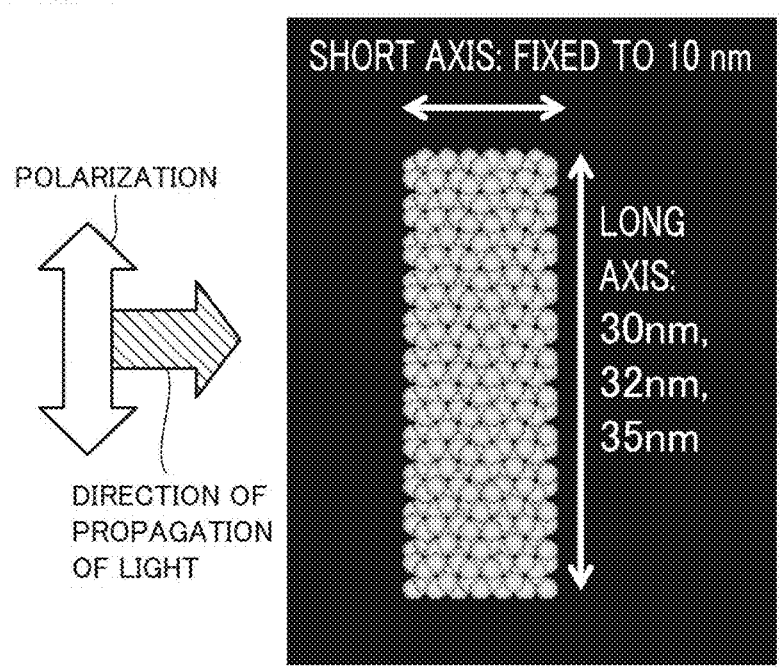
FIG. 17 shows a three-dimensional model (in the form of a column) of the gold nanorod shown in FIG. 16.

FIG. 17 shows a three-dimensional model (in the form of a column) of the gold nanorod shown in FIG. 16. With reference to FIG. 17, in this model, the gold nanorod had a short axis set to 10 nm. Furthermore, the gold nanorod had a long axis varied to have lengths of 30 nm, 32 nm and 35 nm. The gold nanorod had its long axis varied in length because experimentally produced gold nanorods (see FIG. 16) have long or short axes varying in length. Furthermore, the model of the gold nanorod is configured of a cluster having a diameter set to 1.5 nm, and a closest packing factor was taken into consideration to complement a gap between spherical clusters to represent a uniform crystal.

Figure 18:
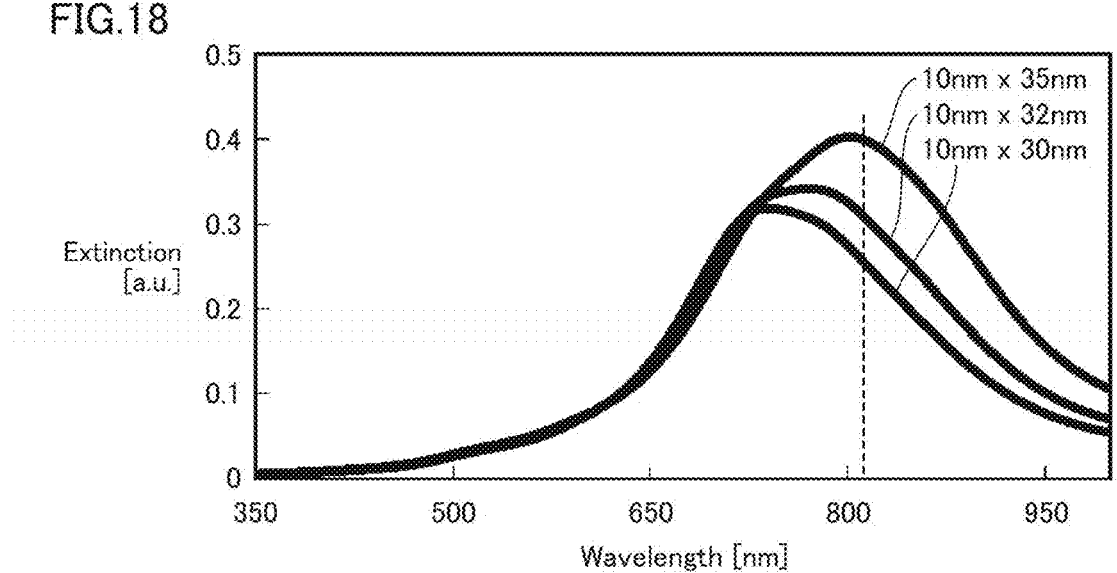
FIG. 18 shows a calculation result of an extinction spectrum by using the three-dimensional model of the gold nanorod shown in FIG. 17.

FIG. 18 shows a calculation result of an extinction spectrum by using the three-dimensional model of the gold nanorod shown in FIG. 17. With reference to FIG. 18, the gold nanorod having a short axis of 10 nm and a long axis of 35 nm presents an extinction spectrum having a peak around a wavelength of 800 nm. A broken line shown in FIG. 18 indicates the position of this peak. A broken line shown in FIG. 15 indicates the position of the wavelength shown in FIG. 18 by the broken line. The peak wavelength indicated in FIG. 18 satisfactorily reproduces the peak wavelength indicated in FIG. 15. This means that the calculation result indicated in FIG. 18 satisfactorily reproduces the experimental result indicated in FIG. 15.

Figure 19:
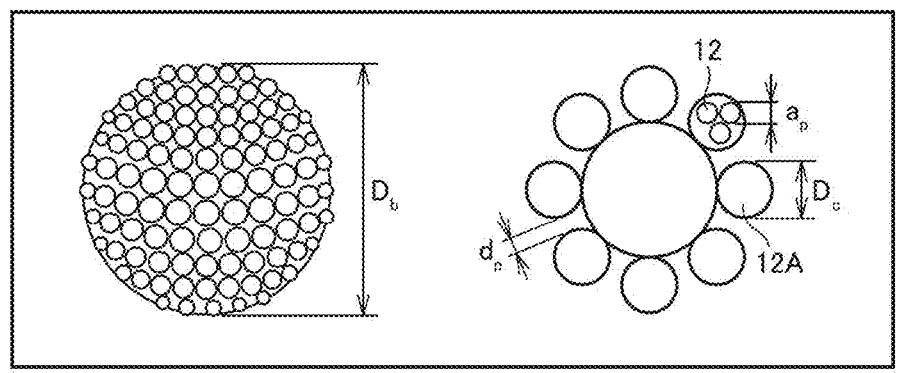
FIG. 19 is a figure for illustrating a three-dimensional model of a bead having metallic nanoparticles fixed thereto.

FIG. 19 is a figure for illustrating a three-dimensional model of a bead having metallic nanoparticles fixed thereto. With reference to FIG. 19, $D_b$ represents a diameter of a metallic nanoparticle assembly structure. $D_c$ represents a diameter of a cluster 12A. $a_p$ represents a diameter of a metallic nanoparticle (metallic nanoparticle 12) configuring cluster 12A. $d_p$ represents an interval between clusters 12A.

Figure 20:
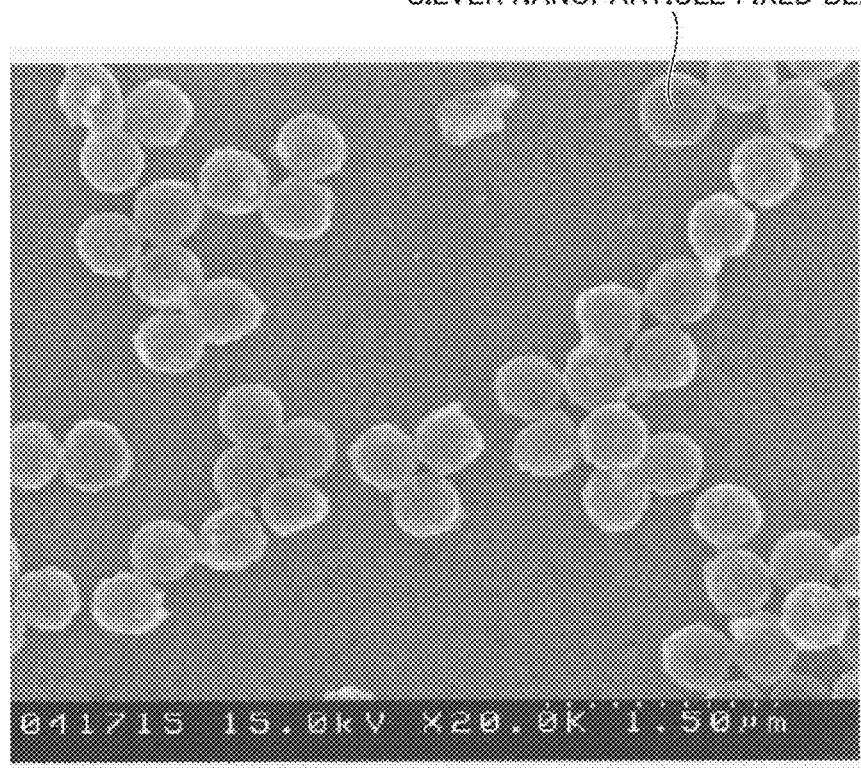
FIG. 20 is an image of a silver nanoparticle fixed bead via an electron microscope.
Figure 21:
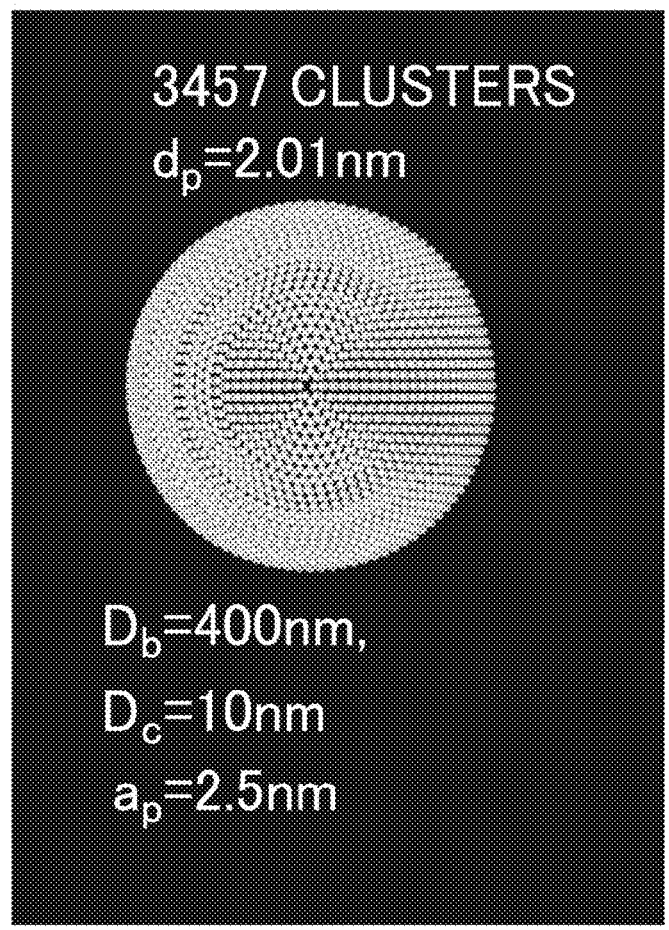
FIG. 21 shows a calculation model of the silver nanoparticle fixed bead shown in FIG. 20.

FIG. 20 is an image of a silver nanoparticle fixed bead via an electron microscope. The single silver nanoparticle fixed bead has approximately 200,000 silver nanoparticles fixed thereto. FIG. 21 shows a calculation model of the silver nanoparticle fixed bead shown in FIG. 20. With reference to FIG. 20 and FIG. 21, the calculation model handles an aggregate of silver nanoparticles as a cluster (a cluster discrete dipole approximation (DDA) method). The FIG. 21 model involves 3457 clusters. Furthermore, $d_p$=2.01 nm, $D_b$=400 nm, $D_c$=10 nm, and $a_p$=2.5 nm.

Figure 22:
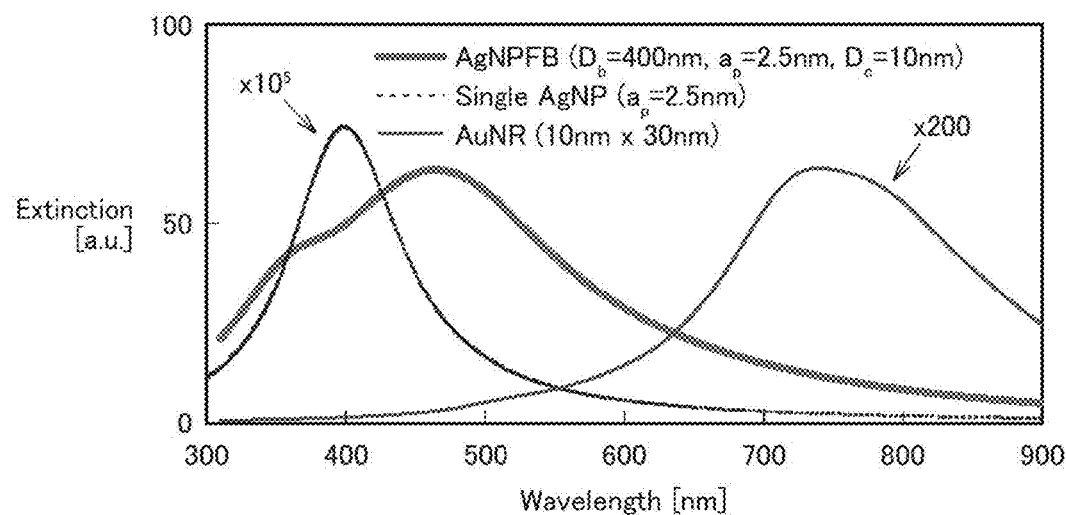
FIG. 22 shows a calculation result of an extinction spectrum of a silver nanoparticle fixed bead and a calculation result of an extinction spectrum of a gold nanorod.

FIG. 22 shows a calculation result of an extinction spectrum of a silver nanoparticle fixed bead and a calculation result of an extinction spectrum of a gold nanorod. FIG. 22 represents an extinction spectrum of a silver nanoparticle fixed bead (AgNPFB), a spectrum obtained by multiplying an extinction spectrum of a gold nanorod (AuNR) by 200, and a spectrum obtained by multiplying an extinction spectrum of a silver nanoparticle (Single AgNP) by $10^5$. The bead's extinction spectrum was calculated with the bead's diameter $D_b$ set to 400 nm, as shown in FIG. 21. In this model, a single cluster includes approximately 64 silver nanoparticles (in volumetric ratio) having a diameter $a_p$ of 2.5 nm. The cluster has a diameter $D_c$ of 10 nm. From these parameters, as well as the FIG. 20 model, the FIG. 21 model presents a silver nanoparticle fixed bead having approximately 200,000 silver nanoparticles fixed thereto.

The gold nanorod's extinction spectrum was calculated with its short axis set to 10 nm and its long axis set to 30 nm. When a single gold nanorod's extinction spectrum is multiplied by 200, it presents a peak substantially equal in height to that of the extinction spectrum of the silver nanoparticle fixed bead. Furthermore, the silver nanoparticle fixed bead's extinction spectrum presents a peak equivalent in height to that of the spectrum obtained by multiplying the extinction spectrum of a single silver nanoparticle (Single AgNP) by $10^5$. From FIG. 22 and FIG. 41, it is expected that the gold nanorod's extinction spectrum can be detected when a single silver nanoparticle fixed bead has gold nanorods on an order of at least 50 in number conjugated thereto via target substance 18.

According to an embodiment of the present invention, localized surface plasmon's extinction spectrum can be measured to detect a trace amount of a target substance. An extinction spectrum is a sum of a scattering spectrum and an absorption spectrum. Accordingly, when discussing where a peak is located, measuring an extinction spectrum is substantially equivalent to measuring a scattering spectrum or measuring an absorption spectrum. In any of the cases, localized surface plasmon presents a substantially identical spectral peak position. Note that the scattering spectrum may be measured or the absorption spectrum may be measured. Hereinafter, a detection device and method according to an embodiment of the present invention will be described in detail.

<Detection Device and Method>

Figure 23:
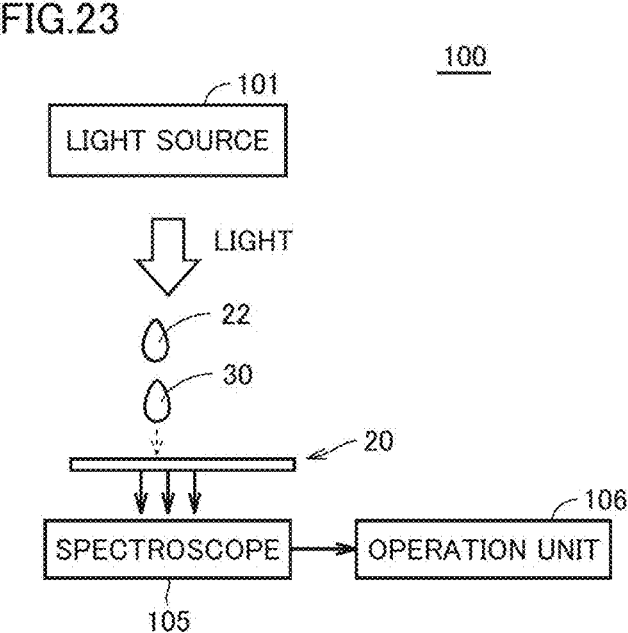
FIG. 23 is a block diagram schematically showing a configuration of a detection device according to one embodiment of the present invention.

FIG. 23 is a block diagram schematically showing a configuration of a detection device according to one embodiment of the present invention. With reference to FIG. 23, a detection device 100 includes a light source 101, a kit 20, a spectroscope 105, and an operation unit 106.

Light source 101 is a light source which emits white light, for example, and it is a halogen lamp, for example. Light source 101 may be implemented as a laser light source. Note, however, that using a white light source as light source 101 allows detection device 100 to be implemented at a low cost. Kit 20 is irradiated with the light (e.g. white light) from light source 101.

Light source 101 may be a light source which emits substantially monochromatic light. The monochromatic light has a wavelength corresponding to that of a peak of localized surface plasmon resonance induced in a metallic nanoparticle assembly structure and metallic nanostructure that are introduced in a sample 30. The wavelength of the monochromatic light is only required to fall within a range in wavelength within twice the peak's full width at half maximum, and the line width of the monochromatic light is not particularly limited. The source of the monochromatic light may for example be a laser light source.

Spectroscope 105 measures an extinction spectrum of localized surface plasmon resonance induced in the metallic nanoparticle assembly structure and metallic nanostructure that are introduced in sample 30 to track how the extinction spectrum of the metallic nanoparticle assembly structure varies when the metallic nanorod conjugates to the metallic nanoparticle assembly structure. Spectroscope 105 outputs a signal indicating a result of the measurement. Preferably, spectroscope 105 is a spectroscope capable of measuring a spectrum in an ultraviolet to near-infrared range (e.g., a wavelength range of 200 nm to 1100 nm). Furthermore, it is preferable that spectroscope 105 has smaller wavelength resolution. For example, the wavelength resolution of spectroscope 105 is equal to or smaller than 10 nm, equal to or smaller than 5 nm, equal to or smaller than 2 nm, or equal to or smaller than 1 nm, however, it is not limited thereto. A conjugate of a single metallic nanoparticle assembly structure and a metallic nanostructure can be observed with a dark field microscope.

Operation unit 106 is implemented as a microcomputer or a personal computer or the like, for example. Operation unit 106 receives the signal from spectroscope 105 (e.g., a signal indicating the intensity of the light detected by spectroscope 105). Operation unit 106 obtains from the extinction spectrum a peak intensity of a short-axis mode of the metallic nanorod conjugate (e.g., peak intensity at a wavelength of 550 nm indicated in FIG. 10 and FIG. 12) and a wavelength of the long-axis mode of the metallic nanorod conjugate (peak intensity at a wavelength of 650 nm). Based on their peak intensity ratio, operation unit 106 detects whether a target substance is present or absent, and/or the substance's concentration.

While FIG. 23 shows light source 101 installed over kit 20 and spectroscope 105 installed under kit 20, light source 101 may be installed at the position of spectroscope 105 and operation unit 106 shown in the figure and spectroscope 105 and operation unit 106 may be installed at the position of light source 101 shown in the figure.

Figure 26:
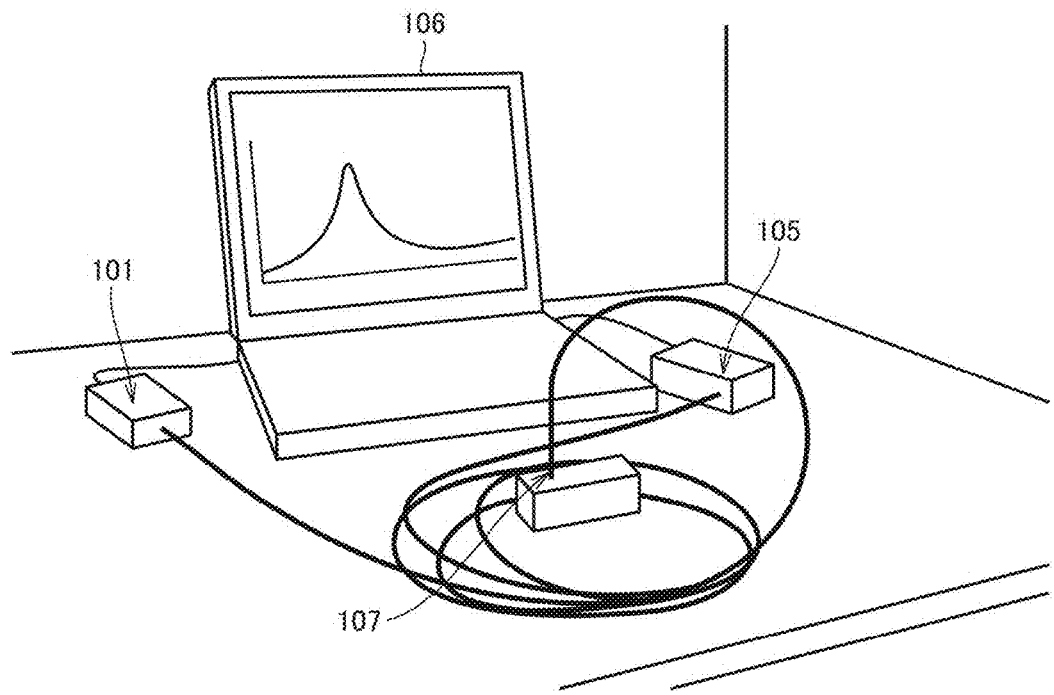
FIG. 26 shows a configuration of a detection device according to one embodiment of the present invention.
Figure 27:
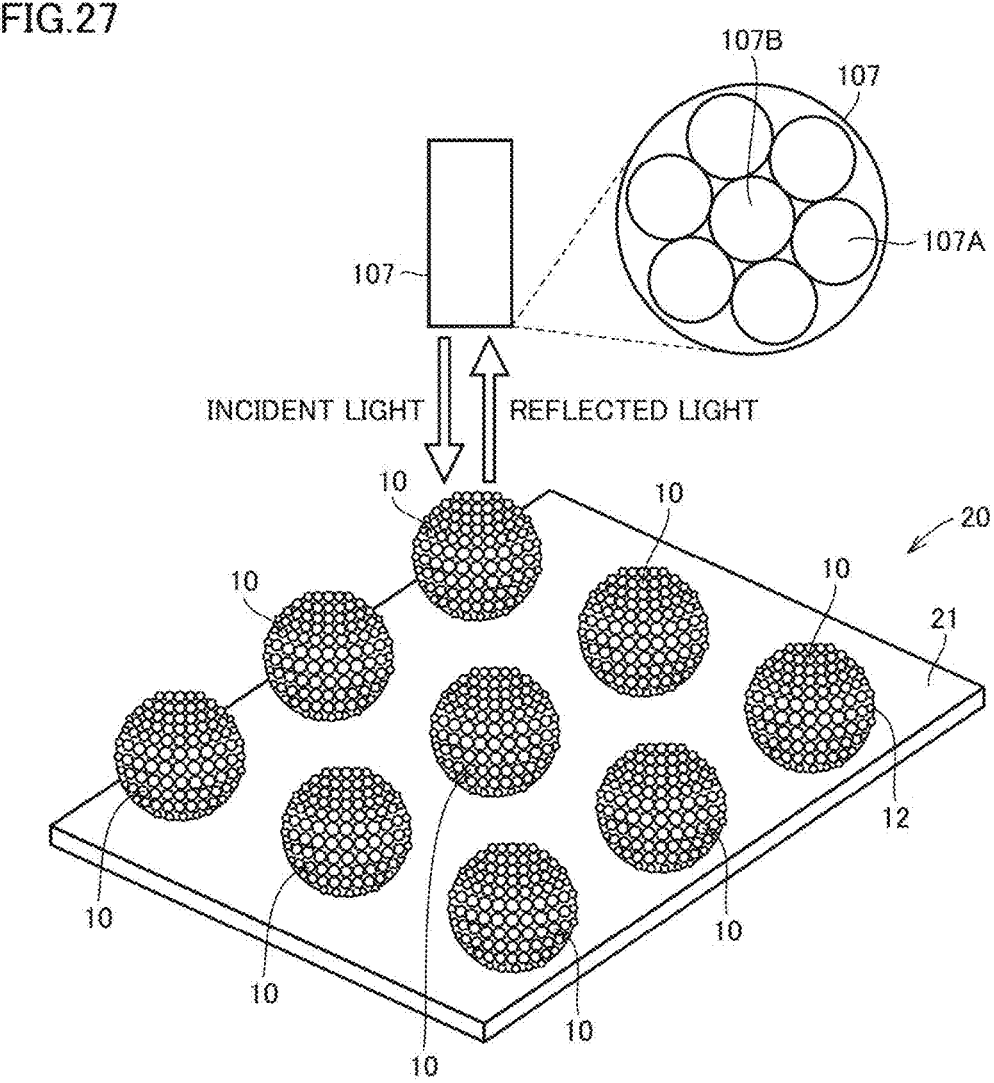
FIG. 27 is a schematic diagram for illustrating how a substance is detected using an optical probe 107 shown in FIG. 26.

Furthermore, although not shown in FIG. 23, optics (e.g., a mirror, a lens, an optical fiber, and the like) may additionally be introduced to guide white light or monochromatic light from light source 101 to kit 20. As shown in FIG. 26 and FIG. 27, similarly, optics such as optical fiber may additionally be introduced to guide reflection of light from kit 20 to the spectroscope.

In one embodiment, the metallic nanoparticle assembly structure is a bead having gold nanoparticles fixed thereto. A substrate and metallic nanoparticle assembly structure 10 fixed to the substrate configure kit 20.

Figure 24:
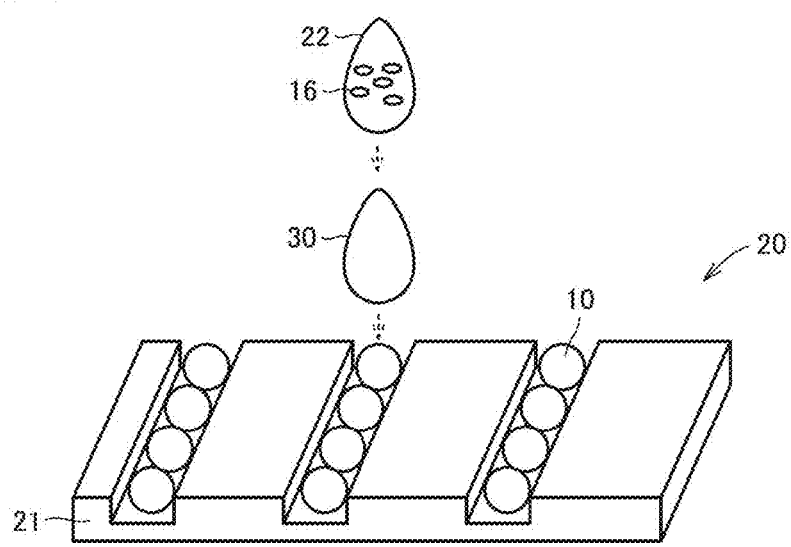
FIG. 24 schematically shows a metallic nanoparticle assembly structure fixed to a kit.

FIG. 24 schematically shows a metallic nanoparticle assembly structure fixed to a kit. With reference to FIG. 24, kit 20 includes a substrate 21 having a grooved structure. For example, substrate 21 is polydimethylsiloxane (PDMS) film. PDMS is a type of silicone rubber and is moldable or the like to easily form a microstructure. Accordingly, as shown in FIG. 24, a grooved structure suitable for a particle diameter of metallic nanoparticle assembly structure 10 is formed on the PDMS film and that groove receives metallic nanoparticle assembly structure 10.

Furthermore, kit 20 may have substrate 21 of a single glass plate or similarly formed of a material that is transparent for white light. Preferably, substrate 21 is for example formed using silicon, quartz or a similar material that does not affect localized surface plasmon resonance and does not present anisotropy for polarization. If the single glass plate is used as substrate 21, a silane coupling agent is utilized to introduce mercapto group or amino group. Thus, metallic nanoparticle assembly structure 10 (or a bead) is captured on substrate 21 chemically or electrostatically.

Gold nanoparticles are fixed to a bead for example by the following method. Initially, gold nanoparticle dispersion and a bead are introduced in into a binder. The binder is an aqueous or ethanol solution of alkylthiol, for example. This solution is agitated at room temperature. The solution is initially red in color, and as it is agitated it varies in color to be transparent (or colorless). After the solution has become transparent, it is continuously agitated for a prescribed period of time. A gold nanoparticle assembly structure is thus produced.

A gold nanoparticle fixed bead is modified with a host molecule for example in the following method:

For example, if the host molecule is avidin, the gold nanoparticle fixed bead is initially dispersed in a phosphoric acid buffer (20 mM, pH 7.4). 1 mM of dithiodipropionic acid (DDA) is mixed into the buffer, and the buffer is agitated for 1 hour. Then, 1-ethyl-3 (3-dimethylaminopropyl)carbimide (EDC) is mixed into the buffer and it is agitated for 1 hour. Subsequently, 100 mM of N-hydroxysuccinimide (NHS) is mixed into the buffer and it is agitated for 1 hour. Subsequently, streptavidin (100 µg/mL) is mixed into the buffer, and it is agitated for 1 hour (see Analytical Chemistry, Vol. 77, No. 21, Nov. 1, 2005, pp. 6976-6984 for example).

Furthermore, if the host molecule is DNA, then for example the following method is applicable. Initially, 3.61 µM of thiolated DNA is added to a liquid having a gold nanoparticle fixed bead dispersed therein, and the liquid is then allowed to stand for example for 16 hours. Sodium chloride and a phosphoric acid buffer (pH: 7.0) are added to the above solution to be 0.1 M and 10 mM and the solution is then allowed to stand for example for 40 hours. Centrifugation is performed to settle nanoparticles and cleaning is performed.

Furthermore, the gold nanorod is prepared for example in the following method: Initially, 50 mL of an aqueous solution of cetyltrimethylammonium bromide (CTAB) (0.2 M) is prepared. Then, a growth solution for the gold nanorod is prepared. Specifically, an aqueous solution of silver nitrate (e.g., 0.01 M, 100 µL), $HAuCl_4$ (0.01 M, 500 µL), and an aqueous solution of ascorbic acid (0.1 M, 55 µL) are mixed in this order into 5 mL of the CTAB solution, and the ascorbic acid reduces gold ions to precipitate gold. Then, a seed solution for the gold nanorod is prepared. Specifically, for example, a $HAuCl_4$ solution (0.01 M, 500 µL) and a sufficiently cooled aqueous solution of $NaBH_4$ (300 µL, 0.01 M) are mixed into the CTAB solution (5 mL). The seed solution (12 µL) is mixed with the growth solution to grow a gold nanorod. In doing so it is preferable to maximally avoid agitation. The nanorod has a size substantially proportional to the growth time. After a prescribed period of time has elapsed, the solution is washed away to cease growing the gold nanorod.

The gold nanorod may have any aspect ratio that is larger than one. Furthermore, the gold nanorod may have a short axis of any length. For example, in view of helping to prepare the gold nanorod, it is preferable that the gold nanorod should have a short axis equal to or larger than 10 nm.

Furthermore, the gold nanorod can be modified with a host molecule in the same method as modifying a gold nanoparticle fixed bead with a host molecule. Accordingly, the method for modifying the gold nanorod with the host molecule will not be described specifically. As described above, sample 30 and metallic nanorod dispersion 22 are dropped on kit 20 to introduce a metallic nanoparticle assembly structure and a metallic nanorod into sample 30.

Figure 25:
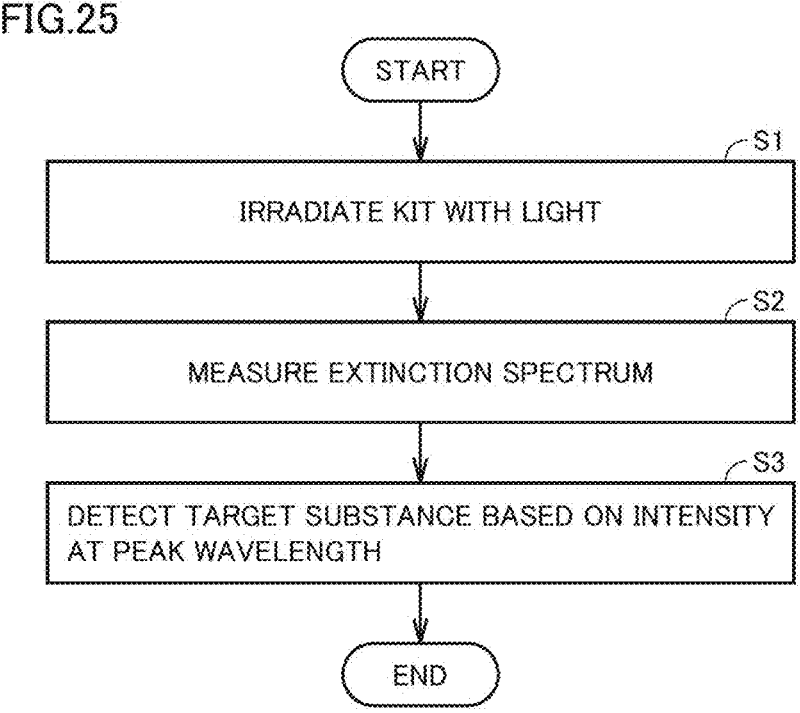
FIG. 25 is a flowchart for illustrating a method for detecting a target substance according to one embodiment of the present invention.

FIG. 25 is a flowchart illustrating a method for detecting a target substance according to one embodiment of the present invention. With reference to FIG. 23 and FIG. 25, in Step S1, kit 20 is irradiated with light (white light or monochromatic light) output from light source 101. In Step S2, spectroscope 105 measures an extinction spectrum of localized surface plasmon resonance of metallic nanoparticle assembly structure 10 and a metallic nanorod. If a metallic nanorod conjugate has been formed, the extinction spectrum presents a component attributed to the long-axis mode of the metallic nanorod conjugate and a component attributed to the short-axis mode of the metallic nanorod conjugate.

In Step S3, operation unit 106 detects a target substance, as based on intensity at a peak wavelength of the extinction spectrum. For example, a preliminary experiment is performed to measure a relationship between the concentration of the target substance in a sample and a signal intensity ratio in the extinction spectrum. Operation unit 106 stores this relationship previously for example as a table. Operation unit 106 calculates a signal intensity ratio from a result of a measurement done by spectroscope 105. Operation unit 106 detects the target substance if the calculated signal intensity ratio exceeds a reference value. The reference value is previously set according to the above table.

Note that operation unit 106 may use a relationship defined in the above table and a signal intensity ratio obtained from a result of a measurement done by spectroscope 105 to calculate the target substance in concentration. Furthermore, a result of a preliminary experiment may be used to determine a function for deriving a target substance's concentration from a signal intensity ratio, and operation unit 106 may use the function and the intensity of a signal measured by spectroscope 105 to calculate the concentration of the target substance.

FIG. 26 shows a configuration of a detection device according to one embodiment of the present invention. With reference to FIG. 26, light source 101 emits light which is in turn directed by an optical probe 107 so that a kit is irradiated thereto. The kit provides a reflection of the light, which is in turn guided by optical probe 107 to spectroscope 105. Operation unit 106 is implemented as a personal computer. The personal computer receives a signal from spectroscope 105 and processes the signal. Spectroscope 105 is a portable spectroscope. For example, USB4000, a product of Ocean Optics. Inc can be used as spectroscope 105.

FIG. 27 is a schematic diagram for illustrating how a substance is detected using optical probe 107 shown in FIG. 26. With reference to FIG. 27, optical probe 107 includes optical fibers 107A and 107B. Optical fiber 107A transmits light from light source 101 to be incident on metallic nanoparticle assembly structure 10. Optical fiber 107B receives a reflection of light from metallic nanoparticle assembly structure 10 and transmits it to spectroscope 105.

Substrate 21 has a plurality of metallic nanoparticle assembly structures 10 disposed thereon. For example, each metallic nanoparticle assembly structure 10 is provided with an individual analyte. To avoid cumbersomeness, FIG. 27 does not show the gold nanorod. For example, optical probe 107 or kit 20 is scanned to irradiate a single metallic nanoparticle assembly structure 10 with the light of the light source to obtain a reflection of light from that metallic nanoparticle assembly structure 10. This allows a target substance to be detected for each analyte.

Figure 28:
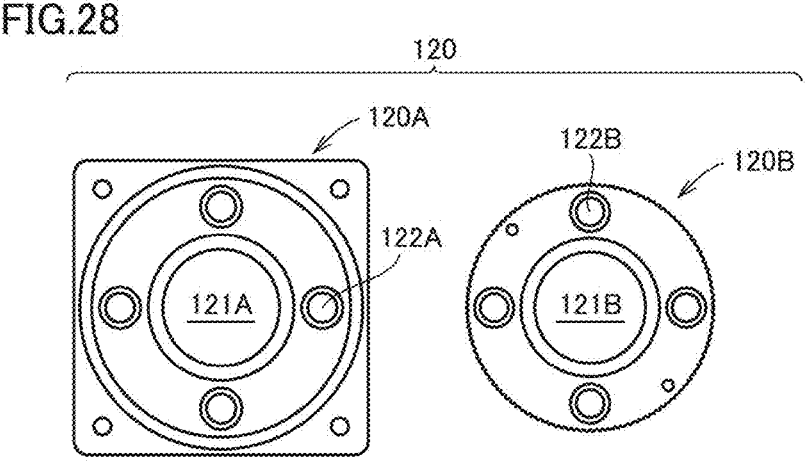
FIG. 28 is an exploded view showing one example of a holder for holding a substrate to which the metallic nanoparticle assembly structure is fixed.

FIG. 28 is an exploded view showing one example of a holder for holding a substrate to which a metallic nanoparticle assembly structure is fixed. With reference to FIG. 28, holder 120 includes a base 120A and a pressing member 120B. Base 120A has an opening 121A and a recess 122A. Pressing member 120B has an opening 121B and a projection 122B. Base 120A and pressing member 120B are formed of metal (e.g., stainless steel or the like).

Figure 29:
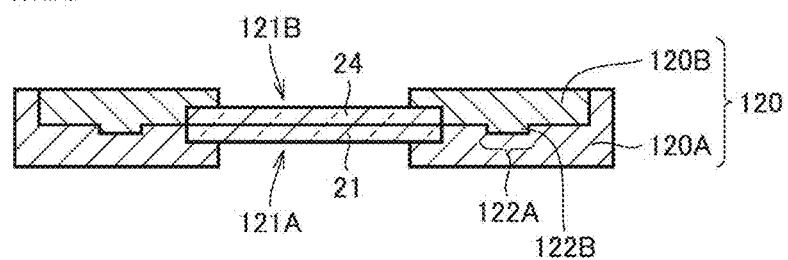
FIG. 29 shows a substrate 21 held by a base 120A and a pressing member 120B shown in FIG. 28.
Figure 30:
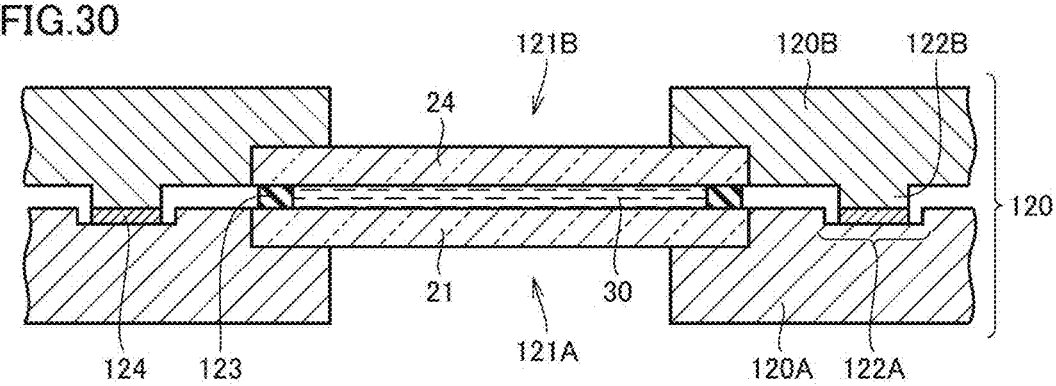
FIG. 30 is an enlarged view generally showing a vicinity of an opening of a holder 120 shown in FIG. 29.

FIG. 29 shows substrate 21 held by base 120A and pressing member 120B shown in FIG. 28. FIG. 30 is an enlarged view generally showing a vicinity of an opening of holder 120 shown in FIG. 29. With reference to FIG. 29 and FIG. 30, substrate 21 is attached to base 120A at opening 121A. A glass cover 24 is attached to pressing member 120B at opening 121B. Sample 30 is introduced into a gap formed between glass cover 24 and substrate 21. In order to prevent leakage of sample 30, a packing 123 is provided between glass cover 24 and substrate 21. The pressing member 120B projection 122B is inserted into the base 120A recess 122A. Projection 122B has an end provided with a magnet 124. Magnet 124 and base 120A attract each other to secure pressing member 120B.

Thus, according to one embodiment of the present invention, a target substance is detected based on a peak of an extinction spectrum of localized surface plasmon resonance caused when a metallic nanoparticle assembly structure and a metallic nanorod are conjugated by the target substance. Even if the target substance is present in a trace amount, the metallic nanorods conjugated to the metallic nanoparticle assembly structure allow an extinction spectrum to be presented with a peak attributed to the metallic nanorods. Accordingly, even if the target substance is present in a trace amount, the target substance can be detected. The detection device and method according to the present embodiment can thus detect a trace amount of a target substance.

Furthermore, the decrease of size of the metallic nanoparticle assembly structure allows the target substance to be detected more efficiently. In addition, the detection device's cost can be reduced.

To detect a trace amount of a target substance, it is preferable that the metallic nanorod be conjugated to the metallic nanoparticle assembly structure as efficiently as possible. In contrast, in view of cost, it is preferable that the metallic nanoparticle assembly structure be reduced in size and that the metallic nanoparticle assembly structure and the metallic nanorod be minimized in amount. In order to address such an issue, the metallic nanoparticle assembly structure and the metallic nanorod may be collected by applying a method of arranging metallic nanoparticles by polarization, as described for example in Japanese Patent Application No. 2010-227627. Hereinafter the method described in Japanese Patent Application No. 2010-227627 will be outlined.

Figure 31:
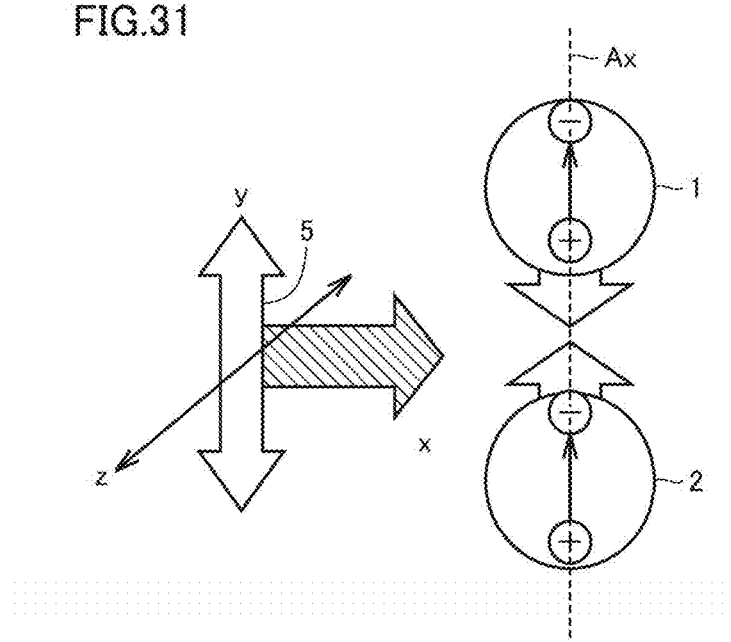
FIG. 31 is a figure for illustrating attractive force acting between two metallic nanoparticles by light induced force.

FIG. 31 is a figure for illustrating attractive force acting between two metallic nanoparticles by light induced force. With reference to FIG. 31, particles 1 and 2 are arranged in the y-direction. An axis Ax represents an axis passing through particles 1 and 2 through their respective centers.

Polarized light 5 is incident on particles 1 and 2. Polarized light 5 has a direction of polarization in the y-direction. In other words, polarized light 5 is polarized in a direction parallel to axis Ax passing through particles 1 and 2 through their respective centers. In that case, particles 1 and 2 are each polarized in a direction parallel to the direction of polarization of polarized light 5. Negative force acts on particle 1, whereas positive force acts on particle 2. Accordingly, attractive force acts between particles 1 and 2.

Figure 32:
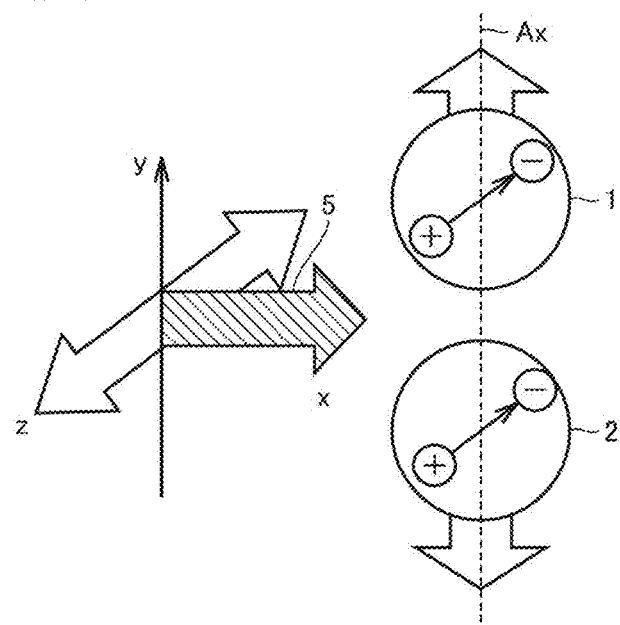
FIG. 32 is a figure for illustrating repulsive force acting between two metallic nanoparticles by light induced force.

FIG. 32 is a figure for illustrating repulsive force acting between two metallic nanoparticles by light induced force. With reference to FIG. 32, polarized light 5 polarized in a direction perpendicular to axis Ax is incident on particles 1 and 2. Particles 1 and 2 are each polarized in a direction parallel to the direction of polarization of polarized light 5. In other words, particles 1 and 2 are polarized in a direction perpendicular to axis Ax of particles 1 and 2. As particles 1 and 2 are polarized in mutually same directions, repulsive force arises between particles 1 and 2.

Thus polarization provided in a controlled direction allows force (attractive force and repulsive force) caused between two metallic nanoparticles to be controlled. This attractive force or repulsive force can be utilized to arrange metallic nanoparticles.

Figure 33:
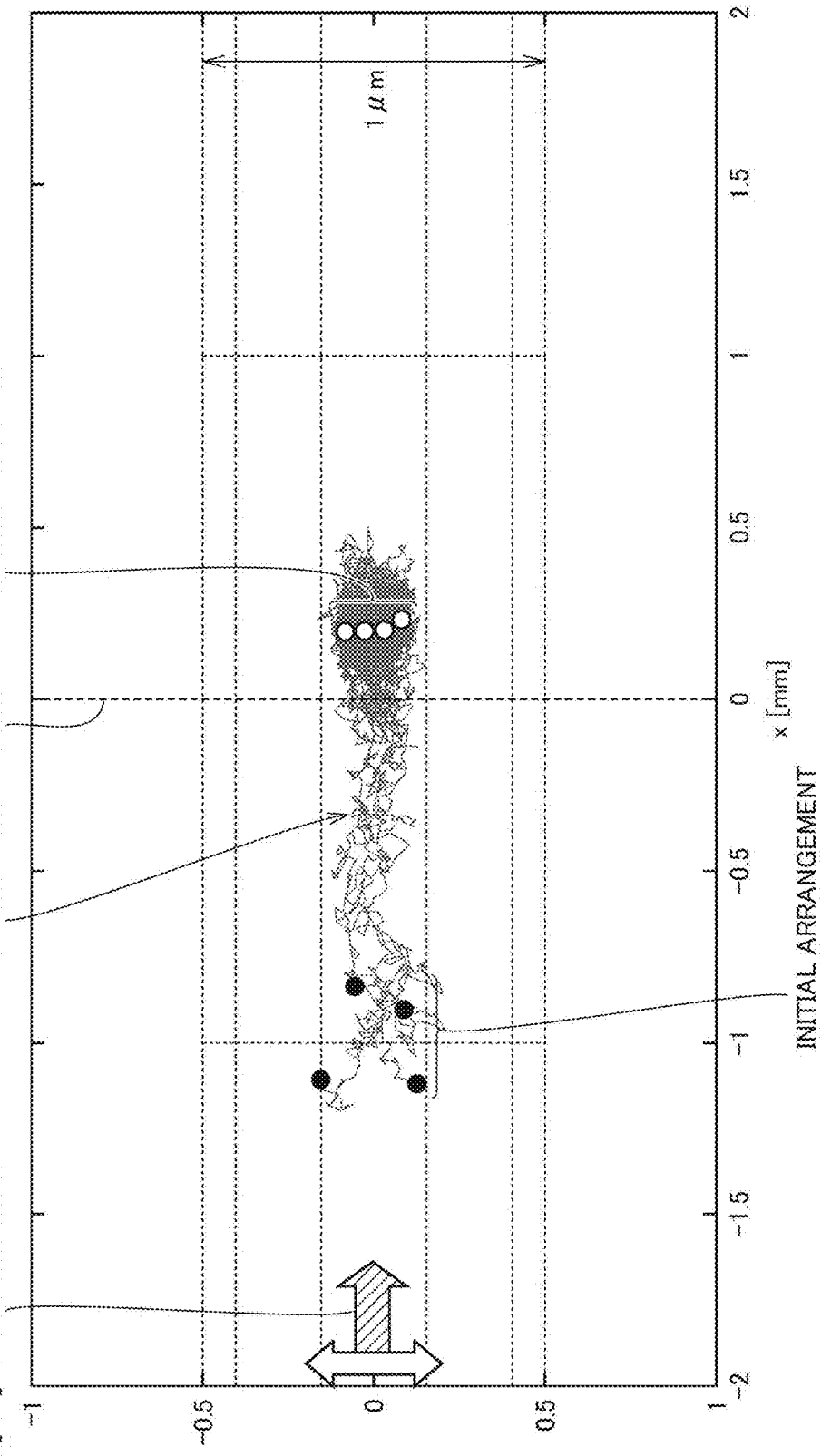
FIG. 33 shows a simulation result of an arrangement of four nanoparticles by polarization.

FIG. 33 shows a simulation result of an arrangement of four nanoparticles by polarization. Note that the metallic nanoparticle was a gold nanoparticle having a diameter of 40 nm. Furthermore, the gold nanoparticle was assumed to be present in water of ordinary temperature. Light intensity of 600 mW was set and an excitation wavelength was set to a non resonant wavelength of 1064 nm. Furthermore, a spot diameter of 1000 nm, a laser light irradiation time of 0.02 s, and 1000000 steps were set (due to a limit in plotting data, a locus of a nanoparticle is plotted every 20 microseconds corresponding to 1000 steps). FIG. 33 shows that four particles can be arranged in a direction parallel to a direction of polarization.

The attractive force or repulsive force that acts between metallic nanoparticles, as has been described above, may be utilized to locally collect metallic nanoparticle assembly structure 10 and metallic nanorod 16.

Figure 34:
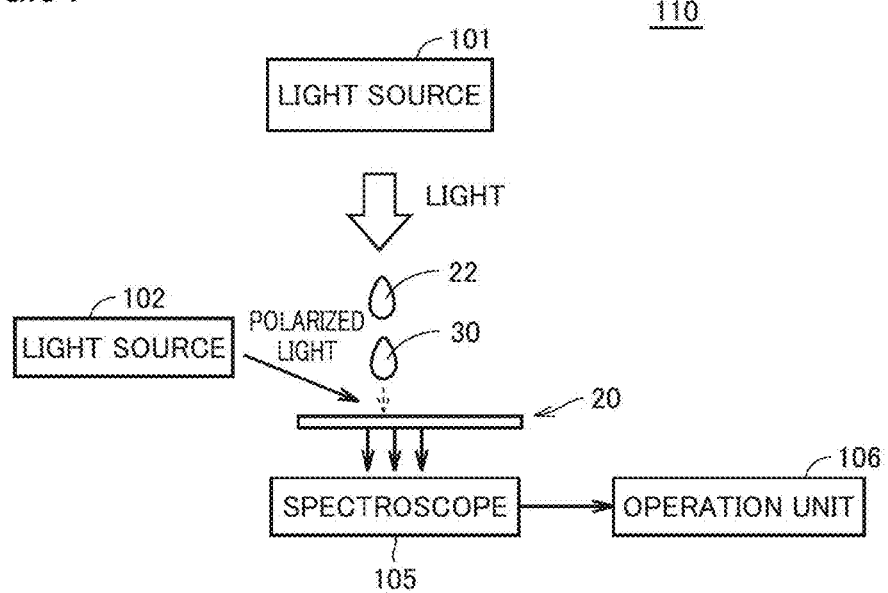
FIG. 34 shows a detection device according to another embodiment of the present invention.

FIG. 34 shows a detection device according to another embodiment of the present invention. With reference to FIG. 34, detection device 110 further includes a light source 102 emitting polarized light. Preferably, light source 102 can change a direction of polarization. Note that polarization is not limited in type to linear polarization, and it may for example be circular polarization, and furthermore, it may be axially symmetric polarization. Note that preferably kit 20 has a surface formed to avoid preventing metallic nanoparticle assembly structure 10 from moving. A liquid having metallic nanoparticle assembly structures dispersed therein may be dropped on a surface of a substrate. Such a substrate can be used as kit 20.

The metallic nanoparticle assembly structure is not fixed to the substrate and instead movable as desired. Accordingly, the metallic nanoparticle assembly structure and the metallic nanorod can be collected by irradiating a specimen having the metallic nanoparticle assembly structure and metallic nanorod introduced therein with polarized light. This allows the metallic nanoparticle assembly structure and the metallic nanorod to be locally increased in density, and a trace amount of a target substance to be detected efficiently. Furthermore, the metallic nanoparticle assembly structure and the metallic nanorod can be used in a small amount to detect the target substance, which contributes to a reduced material cost. A low-cost detection device can thus be achieved.

In another embodiment, a surface enhanced Raman scattering (SERS) spectrum is measured. Kit 20 according to an embodiment of the present invention can be utilized as a substrate for SERS. The SERS spectrum is measured in the same configuration as shown in FIG. 23, FIG. 26, or FIG. 34. Kit 20 may be configured for example as shown in FIG. 24 or FIG. 27.

As shown in FIG. 8, metallic nanoparticle 12 and metallic nanorod 16 conjugated to target substance 18 are irradiated with light. Localized surface plasmon resonance is enhanced in a gap formed between metallic nanoparticle 12 and metallic nanorod 16. That is, an electric field is enhanced in the gap between metallic nanoparticle 12 and metallic nanorod 16. In general, Raman scattering is a third-order nonlinear optical process, and accordingly, Raman scattered light has intensity proportional to the cube of that of the electric field. As the electric field is enhanced, Raman scattered light is significantly increased in intensity. In this embodiment, enhanced Raman scattered light is detected by spectroscope 105. Target substance 18 is thus detected.

Metallic nanoparticle 12 and metallic nanorod 16 may be composed of metal of an identical type. For example, metallic nanoparticle 12 and metallic nanorod 16 are formed of gold. Metallic nanoparticle 12 and metallic nanorod 16 may be formed of metals of different types. For example, metallic nanoparticle 12 is a silver nanoparticle and metallic nanorod 16 is a gold nanorod. A silver nanoparticle allows an electric field to be enhanced more than a gold nanoparticle of the same size, and can thus contribute to an enhanced Raman amplification factor. In an embodiment described hereinafter, metallic nanoparticle 12 is a silver nanoparticle and metallic nanorod 16 is a gold nanorod.

Figure 35:
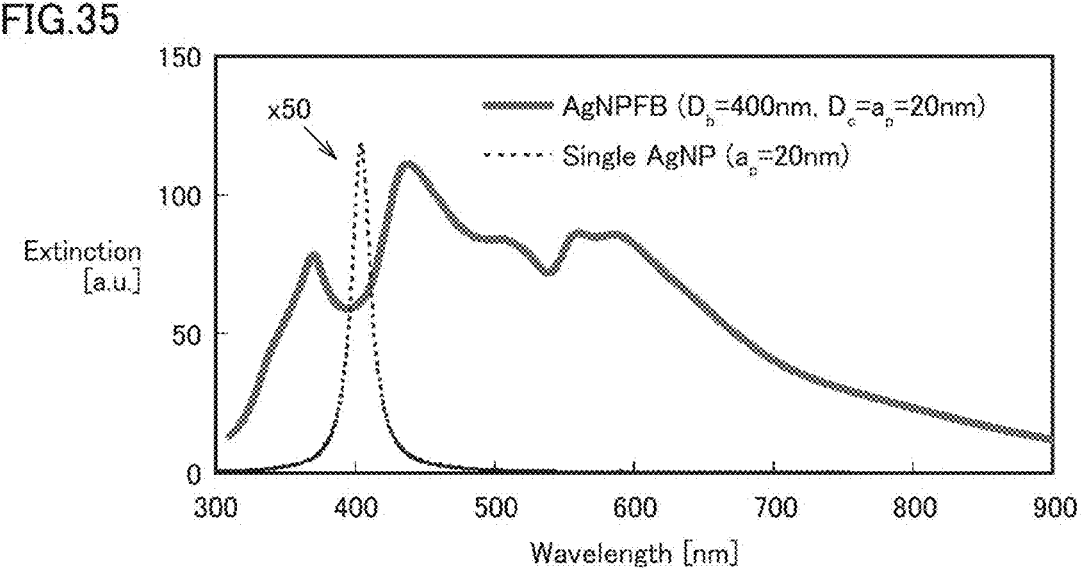
FIG. 35 shows a calculation result of an extinction spectrum by using the model shown in FIG. 19.

FIG. 35 shows a result of calculating an extinction spectrum by using the model shown in FIG. 19, FIG. 35 represents an extinction spectrum of a single silver nanoparticle fixed bead (AgNPFB), and a spectrum obtained by multiplying an extinction spectrum of a single silver nanoparticle (Single AgNP) by 50. In this calculation, the single silver nanoparticle fixed bead's model was set as follows: $D_b$=400 nm and $D_c$=$a_p$=20 nm. In other words, a single cluster is a single silver nanoparticle. There are 1024 clusters, and $d_p$=2 nm.

Furthermore, an effect of electric field enhancement in a core of the silver nanoparticle fixed bead was verified by calculation. An example with no cluster and that with 1024 clusters are compared to examine electric field intensity internal and external to the core for a wavelength of 600 nm. A calculation result indicates that the example with 1024 clusters in comparison with that with no cluster allows an electric field that is enhanced by 1000 times or larger to appear in a vicinity of a surface of the clusters. This indicates that the electric field is enhanced by the entirety of the silver nanoparticles fixed to the bead. As the electric field is enhanced, Raman scattered light is significantly enhanced. A substrate having a silver nanoparticle fixed bead fixed thereto can thus be utilized as a SERS substrate.

Figure 36:
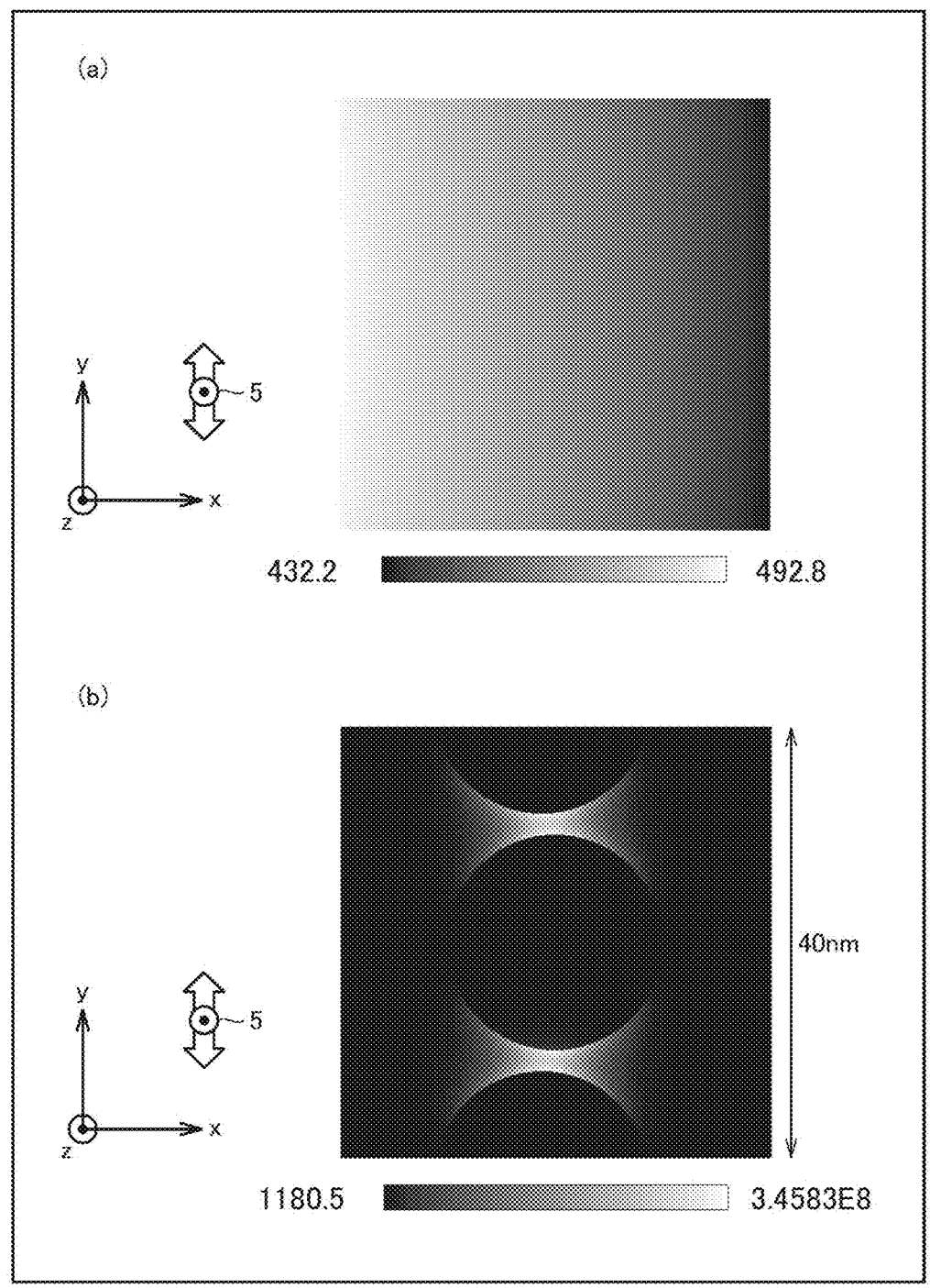
FIG. 36 is a figure for illustrating an effect of electric field enhancement by the silver nanoparticle fixed bead.

FIG. 36 is a figure for illustrating an effect of electric field enhancement by a silver nanoparticle fixed bead. FIG. 36(a) represents electric field intensity of a core in a case only with an incident electric field (with no clusters). FIG. 36(b) represents electric field intensity of a core in a case with $d_p$=2 nm and 1024 clusters. FIG. 36 is an enlarged view of electric field intensity distribution for a wavelength $\lambda$=600 nm in an x-y plane with the bead's center serving as an origin.

FIG. 36 represents that a gap (a nanogap) between metallic nanoparticles enhances electric field intensity almost 1 million times. This means that SERS is enhanced in intensity by the nanogap by almost $10^{18}$ times by the principle of enhancement of electric field intensity described above. An analyte smaller than the nanogap can be detected with high sensitivity.

A silver nanoparticle on a surface of a bead and a gold nanorod with a gap in an order of 10 nm also allow an electric field to be effectively enhanced, as will now be described hereinafter.

Figure 37:
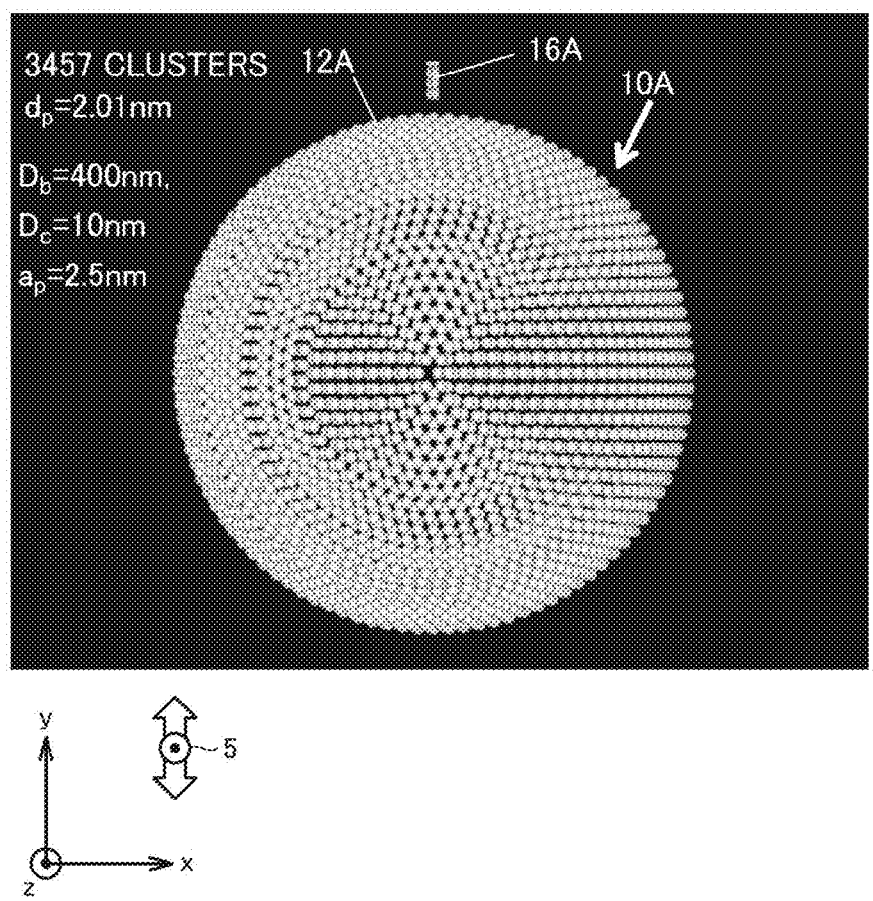
FIG. 37 is a figure for illustrating a three-dimensional model having metallic nanorod 16 fixed by the metallic nanoparticle assembly structure.
Figure 38:
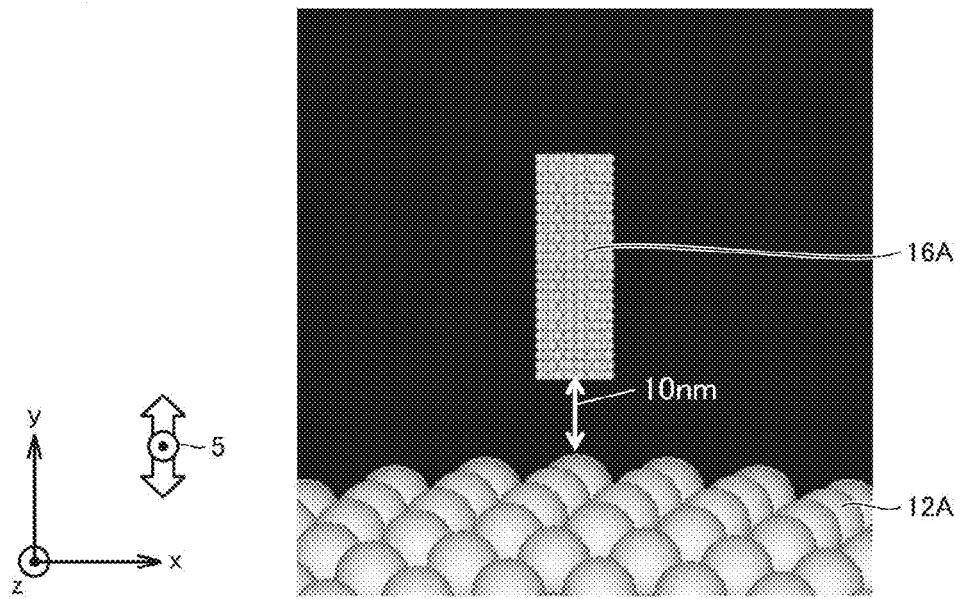
FIG. 38 is an enlarged view of the model shown in FIG. 37.

FIG. 37 is a figure for illustrating a three-dimensional model having metallic nanorod 16 fixed by a metallic nanoparticle assembly structure. FIG. 38 is an enlarged view of the model shown in FIG. 37. With reference to FIG. 37 and FIG. 38, a metallic nanoparticle assembly structure 10A is a bead having a surface with a cluster 12A fixed thereto, cluster 12A being formed of an aggregate of silver nanoparticles. $d_p$=2.01 nm, $D_b$=400 nm, $D_c$=10 nm, and $a_p$=2.5 nm. Metallic nanoparticle assembly structure 10A has 3457 clusters. Cluster 12A is spherical in geometry. Gold nanorod 16A is the gold nanorod shown in FIG. 17. In this model, the gold nanorod had a long axis set to have a length of 30 nm and a short axis set to have a length of 10 nm. The gold nanorod is configured of a cluster having a diameter of 1.5 nm. Furthermore, a closest packing factor was considered, similarly as done in the calculations in FIG. 17 and FIG. 18. The gold nanorod has 919 clusters. While gold nanorod 16A and cluster 12A in this embodiment had a distance therebetween set to 10 nm, it depends on the sizes of the antigen, antibody and analyte, and its shortest distance is 2 nm.

Figure 39:
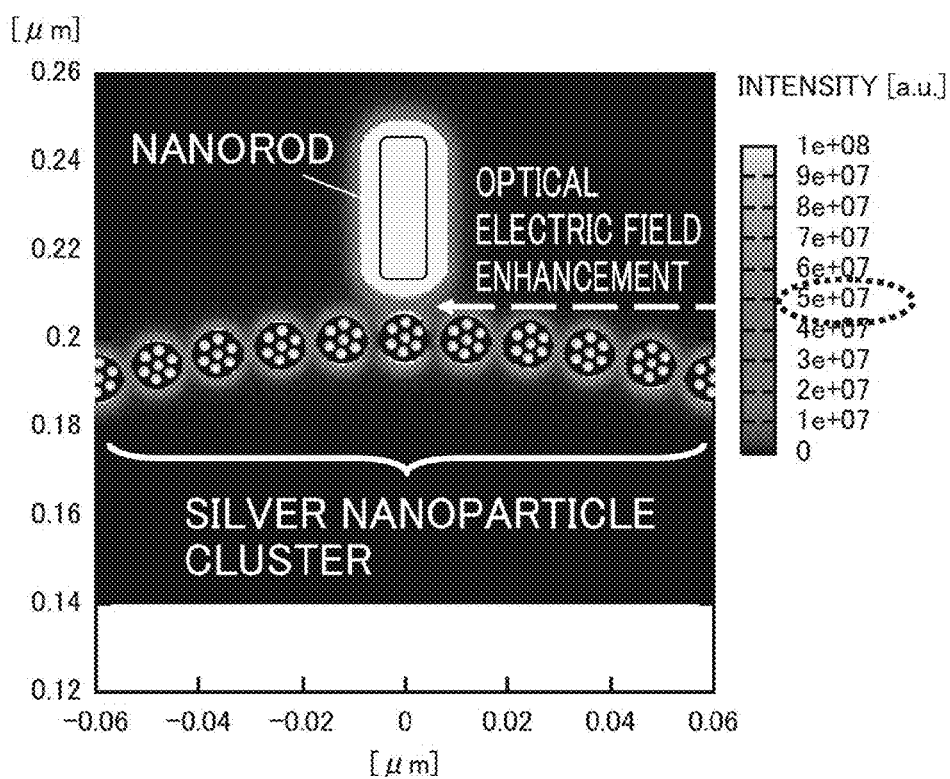
FIG. 39 shows a calculation result of the intensity of an optical electric field enhanced by the models shown in FIGS. 37 and 38.
Figure 40:
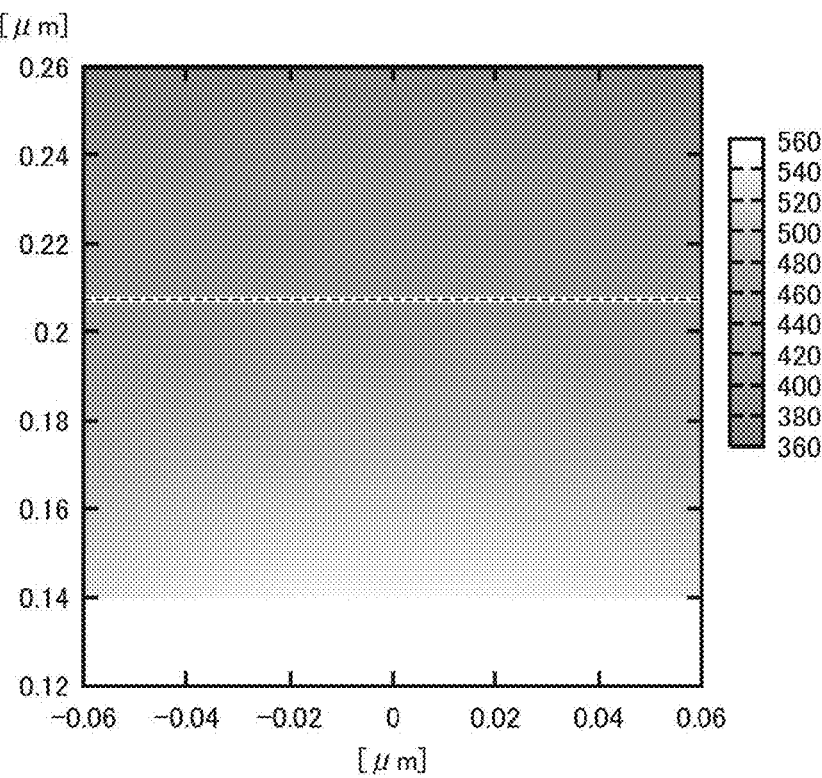
FIG. 40 shows a calculation result of the intensity of an optical electric field resulting from incident light alone.

FIG. 39 shows a calculation result of the intensity of an optical electric field enhanced by the models shown in FIGS. 37 and 38. FIG. 40 shows a calculation result of the intensity of an optical electric field resulting from incident light alone. In FIG. 39 and FIG. 40, the excitation wavelength is close to a peak of a metallic nanorod, or 800 nm. The incident light is a Gaussian beam polarized along the long-axis of the rod (or in the y-direction) and proceeds in a direction perpendicular to the plane of the drawing (or the z-direction). Note that the incident light's spot had a radius set to 500 nm. FIG. 39 and FIG. 40 represent an optical electric field in intensity in the x-y plane (z=0).

As shown in FIG. 39, a gap between gold nanorod 16A and cluster 12A of silver nanoparticles, or a nanogap, presents an electric field with an intensity of approximately $5 \times 10^7$. In contrast, for incident light alone, a y-coordinate that is the same as the nanogap, which is indicated by a broken line, presents an electric field with an intensity of approximately 450. Accordingly, between gold nanorod 16A and cluster 12A, incident light's optical electric field intensity is enhanced approximately 100000 times. This means that if a target substance exists between gold nanorod 16A and cluster 12A Raman scattered light from the substance is enhanced $10^{15}$ times or larger.

Figure 41:
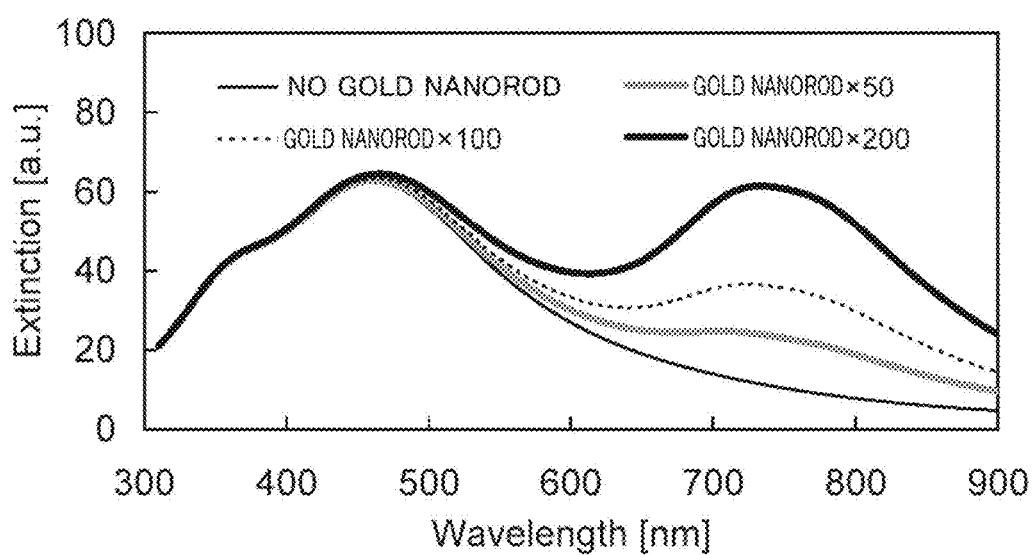
FIG. 41 represents a silver nanoparticle fixed bead with different numbers of gold nanorods conjugated thereto presenting differently peaking extinction spectra.

FIG. 41 represents a silver nanoparticle fixed bead with different numbers of gold nanorods conjugated thereto presenting differently peaking extinction spectra. The extinction spectra were calculated using the models represented in FIG. 37 to FIG. 39. With reference to FIG. 41, "no gold nanorod" represents a spectrum of the silver nanoparticle fixed bead alone. "Gold nanorod×50", "gold nanorod×100" and "gold nanorod×200" represent an extinction spectrum alone of the portion of the gold nanorod that is multiplied by 50, 100 and 200, respectively. These spectra correspond to a spectrum of a model in which a silver nanoparticle fixed bead has an upper surface (a surface opposite to a substrate) with gold nanorods conjugated thereto by an antigen-antibody reaction (see FIG. 37). As the silver nanoparticle fixed bead has more gold nanorods conjugated thereto, a peak in a range in wavelength around 700 nm to 800 nm increases.

Figure 42:
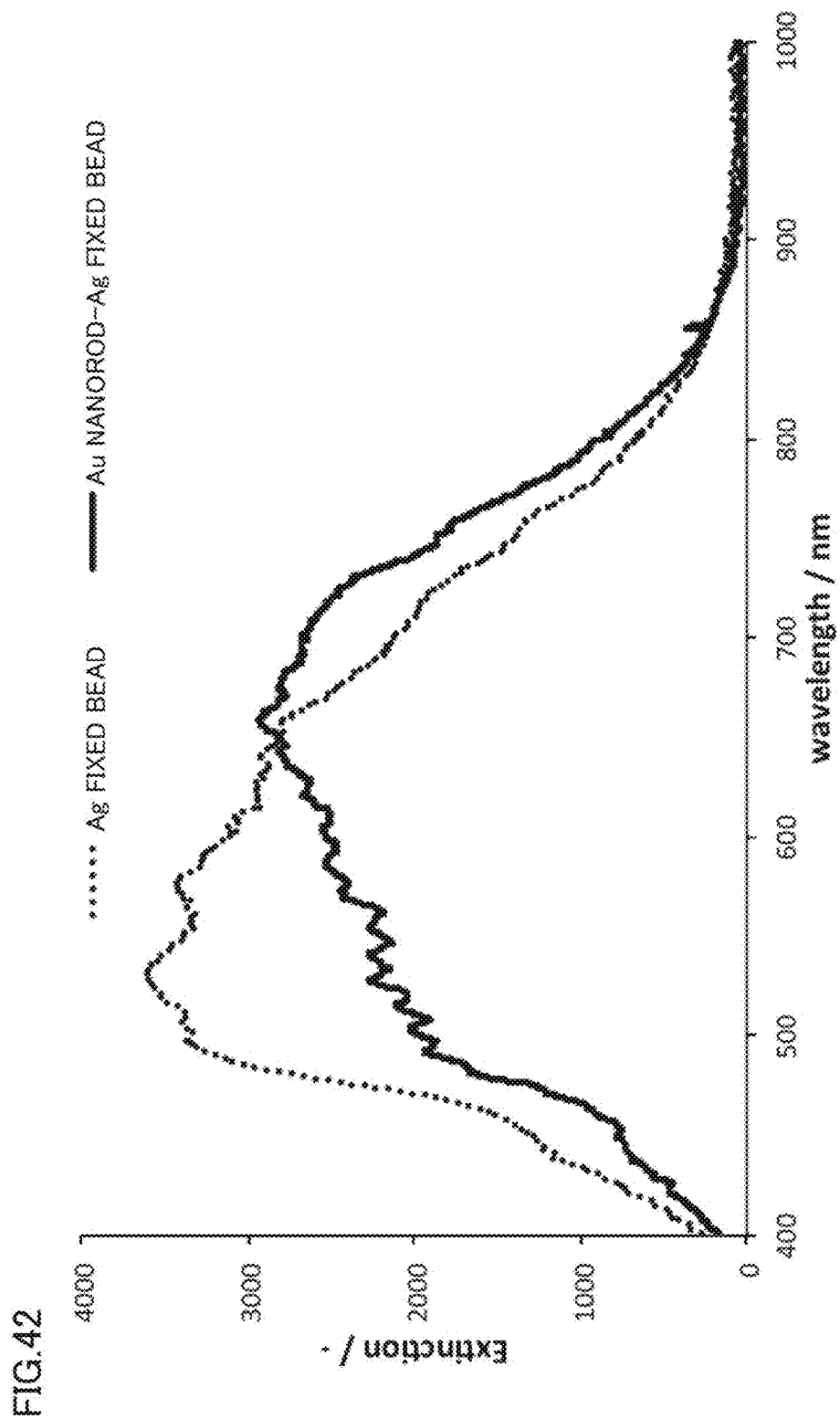
FIG. 42 shows an extinction spectrum obtained by observing a set of a conjugate of a silver nanoparticle fixed bead and gold nanorods with a dark field microscope.

FIG. 42 shows an extinction spectrum obtained by observing a set of a conjugate of a silver nanoparticle fixed bead and a gold nanorod with a dark field microscope. The silver nanoparticle fixed bead and the gold nanorod are conjugated together by DNA. With reference to FIG. 42, as a plurality of gold nanorods are conjugated to the silver nanoparticle fixed bead, a peak in a range in wavelength around 700 nm to 800 nm increases. FIG. 42 shows that an increased peak of an extinction spectrum has been detected, i.e., that a target substance (herein DNA) has actually been detected. In the present embodiment, it is estimated that a single gold nanorod has a round end face each modified with approximately 7.6 host DNAs, and that a single silver nanoparticle fixed bead has a surface modified with 30,700,000 host DNAs. Furthermore, from a comparison between a theory and an experiment in a wavelength range of 600-900 nm of FIG. 41 and FIG. 42, it is estimated that 50-100 gold nanorods are conjugated to a single silver nanoparticle fixed bead. Accordingly if a target DNA (a target substance) having specifically adhered to all of the host DNAs (or a second host molecule) on an end face of a gold nanorod also specifically adheres to a host DNA (or a first host molecule) on a silver nanoparticle fixed bead, 380-760 target DNAs will have been detected.

In this embodiment the silver nanoparticle fixed bead and the gold nanorod are modified with a host molecule. When the host molecule conjugates to a target substance a nanogap can be formed between the silver nanoparticle bead and the gold nanorod. Accordingly, the present embodiment allows the target substance to be detected by detecting SERS.

In this embodiment the silver nanoparticle fixed bead is fixed to a substrate. Accordingly, the substrate can be used as a SERS substrate.

Furthermore, in this embodiment, any of a light source emitting white light and a light source emitting substantially monochromatic light is applicable. As one example, a commercially available light source provided for Raman scattering and emitting a wavelength around 800 nm used in the above calculation (for example, LuxxMaster® COMPACT RAMAN BOXX®, a product of PD-LD Inc.), can be used.

The silver nanoparticle fixed bead may not be fixed to a substrate. For example, a liquid having silver nanoparticle fixed beads dispersed therein may be prepared.

Furthermore, the SERS described in this embodiment can include surface enhancement resonant Raman scattering (SERRS).

The embodiments disclosed herein are by way of illustration and example in any respect and are not to be taken by way of limitation. The scope of the present invention is interpreted by the terms of the appended claims and intended to encompass any modification within a meaning and range equivalent to the claimed scope.

REFERENCE SIGNS LIST 1, 2: particle; 5: polarization; 6: spot; 10, 10A: metallic nanoparticle assembly structure; 11: bead; 12: metallic nanoparticle; 12A: cluster; 13, 17: host molecule; 16: metallic nanorod; 16A: gold nanorod; 18: target substance; 20: kit; 22: metallic nanorod dispersion; 24: glass cover; 30: sample; 100, 110: detection device; 101, 102: light source; 105: spectroscope; 107: optical probe; 107A, 107B: optical fiber; 121A, 121B: opening; 122A: recess; 122B: projection; 123: packing; 124: magnet; Ax: axis.

The invention claimed is:

1. A detection device for detecting a target substance that may be contained in a specimen, comprising:
    a metallic nanoparticle assembly structure including a bead and a plurality of metallic nanoparticles fixed to a surface of said bead via an interacting site and modified with a first host molecule allowing said target substance to specifically adhere thereto;
    a metallic nanostructure modified with a second host molecule allowing said target substance to specifically adhere thereto, said metallic nanoparticle assembly structure having said plurality of metallic nanoparticles mutually spaced by a distance equal to or smaller than a diameter of said metallic nanoparticle;
    a first light source for irradiating said specimen with light with said metallic nanoparticle assembly structure and said metallic nanostructure introduced in said specimen;
    a second light source configured to irradiate said specimen with polarized light;
    a spectroscope configured for measuring an extinction spectrum of localized surface plasmon resonance of said specimen; and
    a detector for detecting said target substance, based on said spectrum measured with said spectroscope.

2. The detection device for detecting a target substance according to claim 1, further comprising a substrate for fixing said metallic nanoparticle assembly structure thereto.

3. The detection device for detecting a target substance according to claim 1, wherein said metallic nanostructure is a metallic nanorod; and said detector detects said target substance by detecting in said extinction spectrum a peak corresponding to a long-axis mode of a metallic nanorod conjugate, said metallic nanorod conjugate being formed by conjugating said metallic nanorod to said metallic nanoparticle assembly structure.

4. The detection device for detecting a target substance according to claim 3, wherein:

said metallic nanorod has a short axis having a length equal to or larger than 1 nm: and when said metallic nanorod has an aspect ratio defined as a ratio of a long axis of said metallic nanorod to the length of said short axis, said aspect ratio has a value larger than 1.

5. The detection device for detecting a target substance according to claim 3, wherein said metallic nanoparticles of said metallic nanoparticle assembly structure and said metallic nanorods are formed of metals, respectively, identical in type.

6. The detection device for detecting a target substance according to claim 3, wherein said metallic nanoparticles of said metallic nanoparticle assembly structure and said metallic nanorods are formed of metals, respectively, different in type.

7. The detection device for detecting a target substance according to claim 1, wherein:

said target substance is an antigen; and said first and second host molecules are an antibody causing an antigen-antibody reaction with said antigen.

* * * * *